United States Patent [19]

Hazlitt et al.

[11] Patent Number: 4,798,081

[45] Date of Patent: Jan. 17, 1989

[54] HIGH TEMPERATURE CONTINUOUS VISCOMETRY COUPLED WITH ANALYTIC TEMPERATURE RISING ELUTION FRACTIONATION FOR EVALUATING CRYSTALLINE AND SEMI-CRYSTALLINE POLYMERS

[75] Inventors: Lonnie G. Hazlitt, Lake Jackson; Daniel G. Moldovan, Danbury, both of Tex.

[73] Assignee: The Dow Chemical Company, Midland, Mich.

[21] Appl. No.: 137,118

[22] Filed: Dec. 22, 1987

Related U.S. Application Data

[63] Continuation-in-part of Ser. No. 802,354, Nov. 27, 1985, abandoned.

[51] Int. Cl.[4] .............................................. G01N 11/00

[52] U.S. Cl. ...................................... 73/53; 73/61.1 C

[58] Field of Search ..................... 73/61.1 C, 61 R, 53, 73/55

[56] References Cited

U.S. PATENT DOCUMENTS

| | | | |
|---|---|---|---|
| 3,837,217 | 9/1974 | Schulz | 73/53 X |
| 4,258,564 | 3/1981 | Hulme et al. | 73/61.1 C |
| 4,286,457 | 9/1981 | Johnson, Jr. | 73/61.1 C X |
| 4,578,990 | 4/1986 | Abbott et al. | 73/61.1 C X |
| 4,627,271 | 12/1986 | Abbott et al. | 73/61.1 C X |

*Primary Examiner*—Stewart J. Levy

*Assistant Examiner*—Joseph W. Roskos

*Attorney, Agent, or Firm*—Timothy S. Stevens; Nis H. Juhl

[57] ABSTRACT

A method and apparatus for analyzing a solution of a crystalline or a semi-crystalline polymer sample to determine a crystallinity versus weight percent profile concurrently with viscosity average molecular weight. The polymer sample is first precipitated from solution over a cooling temperature gradient to produce a precipitated polymer sample, which is precipitated as a function of its crystallinity. The precipitated polymer sample is then eluted and redissolved over a heating temperature gradient to produce successive fractions of a fractionated polymer sample solution, which are measured to produce concentration and specific viscosity data from which the intrinsic viscosity and viscosity average molecular weight are calculated.

32 Claims, 13 Drawing Sheets

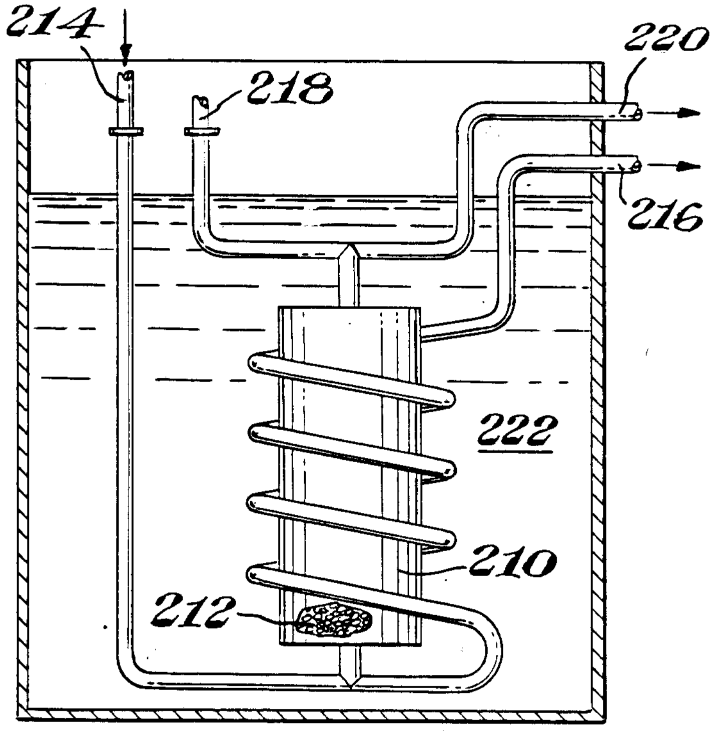
Fig. 4A
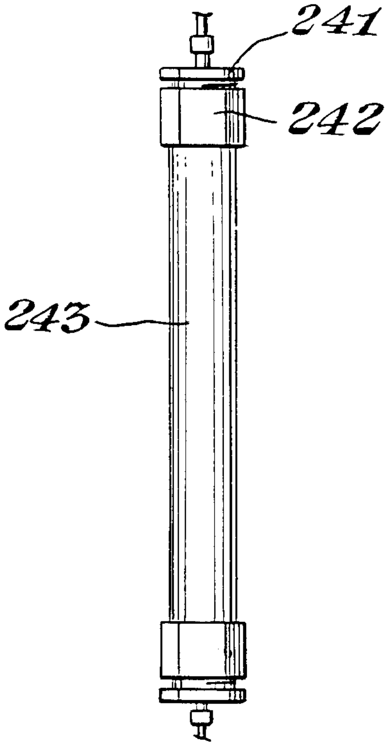
Fig. 4B
Fig. 5
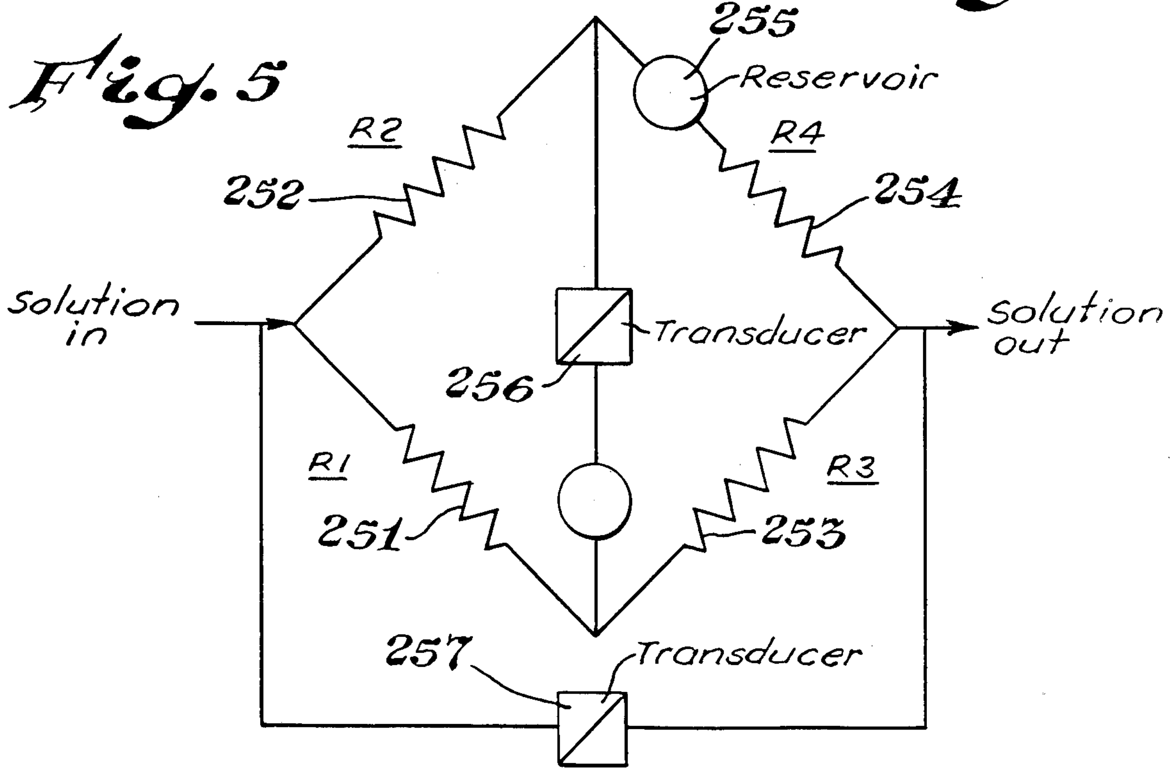

A, B & C - See Fig. 23
Calibration of IR (A) - Recorder Data.
3 consecutive injections of the solutions in Example 6 followed by a repeat of the second injection, because it "saturated" the IR amplifier Raw recorder data-Example 7

ANALYTICAL TEMPERATURE RISING ELUTION FRACTIONATION

HIGH TEMPERATURE CONTINUOUS VISCOMETRY COUPLED WITH ANALYTIC TEMPERATURE RISING ELUTION FRACTIONATION FOR EVALUATING CRYSTALLINE AND SEMI-CRYSTALLINE POLYMERS

CROSS-REFERENCE TO RELATED APPLICATION

This application is a continuation-in-part of Applicants' copending application Ser. No. 802,354, filed Nov. 27, 1985, now abandoned, herein fully incorporated by reference.

FIELD OF THE INVENTION

This invention is directed to method and apparatus for coupling high temperature continuous viscometry (HTCV) with analytical temperature rising elusion fractionation (ATREF) for analysis of crystalline and semi-crystalline polymers. The method and apparatus provide a crystallinity (or density or branching number) versus weight percent profile concurrently with the viscosity average molecular weight for each incremental crystalline fraction. The combination of these two analytical tools into a single instrument provides a powerful means for describing polymer characteristics in terms of crystallinity and molecular weight. The data obtained indicates not only branching frequency, but also viscosity average molecular weight as a function of branching frequency. Further, properties which are a function of comonomer incorporation, i.e. density and crystallinity, can be related to molecular weight.

BACKGROUND OF THE INVENTION

Polymers are basically heterogeneous materials, heterogeneity being exhibited through a variety of ways such as distribution of chain lengths, differences in chemical composition from chain to chain, and through the architecture of the chain as in branched and cross-linked structures. Each form of heterogeneity exerts an influence on the behavior and the properties of the ultimate product.

For semi-crystalline resins such as polyethylene, it is branching which is of particular interest from the point of view of the impact on resin properties and use. Branching, which may be characterized as long chain branching (LCB) or short chain branching (SCB), can arise through chain transfer reactions during free radical polymerization at high pressure or by copolymerization with other comonomers. It is now known that the overall branching level influences resin properties through its control o crystallinity and morphology. Each branch point in a chain disrupts the local order during crystallization and reduces the degree of crystallinity. Thus, there is a direct relationship between crystallinity and the degree of branching. However, while size exclusion chromatography (SEC) provides insight into long chain branching characteristics of crystalline polymers (Lecacheux et al. (I), *J. Ap. Poly. Sci.*, 27:4687-4877 (1982); Lecacheux et al. (II), *J. Ap. Poly. Sci.*, 29:1569-1579 (1984)), size exclusion chromatography leaves much to be desired where short chain branching information is required.

Temperature rising elution fractionation (TREF) is a technique of fractionating a polymer according to crystallinity and has particular utility for evaluating short chain branching. The technique of TREF was first used by Desreux et al., *Bull. Soc. Chim. Belg.*, 59:476 (1950), wherein a 5 gm sample of polyethylene was deposited from toluene solution onto granules and packed into a column. Elution was carried out by flowing toluene through the column as temperature was increased TREF has been employed as a means of studying short chain branched distribution in high pressure, low density polyethylene (LDPE). See Shirayama, K. et al., *Jour Poly Sci.-A*, 3:907 (1955) and Bergstrom, C. et al. *Kemia-Kemi Helsinki*, 23:1, 47 (1976). TREF has been used as well as a means of studying short chain branch distribution in ethylenepropylene copolymers (Solda, S. et al., *Kobunshi Kagaku* (Eng. Ed.), 2, No. 10:866 (1973)) and ethylene-butene copolymers (Wilde, L. et al., (I), *J. Poly. Sci. Poly. Phys. Ed.*, 20:441 (1982); Wilde, L. et al., (II), *Poly. Preprints*, 18(2):182 (1977)); and Wilde, L. et al., (III), *Poly. Preprints*, 23(2):133 (1982)).

From an operative standpoint, TREF (also known as preparative TREF) has certain disadvantages. One is the time required to perform a fractionation, which typically is about seven days. The time-consuming step is the separation of polymers from each of approximately fourteen fractions so that the mass per fraction may be obtained and for further analysis such as determining short chain branching by infrared (IR) analysis. The second deficiency of the preparative procedure involves the manner in which the short chain branching distribution curve is constructed. Due to the limited number of data points available (approximately fourteen), the weight percent distribution profile is not well defined. Also, mass measurements of fractions containing small amounts of polymer are subject to rather large errors because of the difficulty in removing all polymers from the liquid phase during the workup procedure. Further, each of the fractions must be filtered, dried, weighed and pressed into films for analysis. The efficiency of the separation process is less than ideal owing to the large size of the columns, the physical dimensions of the system making it difficult to avoid channeling, "dead" spots, and temperature gradients along the length and across the diameter of the column.

An improvement upon the TREF system, although still requiring the use of preparative TREF for calibration purposes, was the development of analytical temperature rising elution fractionation (ATREF), reported upon by Wilde, L. et al. (I) supra. ATREF overcomes the limitations of preparative TREF by reducing the column (and sample) size considerably and continuously monitoring the amount of polymer eluted as a function of temperature using an in-line detector such as a differential refractometer. On-stream monitoring of polymer concentration at each column elution temperature obviates the need to physically segregate and weigh each fraction collected.

However, branching distribution alone is not sufficient to provide a evaluation of overall resin structure. Wilde, L. et al. (I), supra, proposed to utilize data resulting from an ATREF type analysis in conjunction with separate data produced by size exclusion chromatography to provide an evaluation of overall resin structure. Aside from the complexity of coupling these separate analyses, such an instrument would hardly be a candidate for routine analysis in light of the inherent maintenance requirements for keeping such a device operational. And, while this is an improvement over the preparative method, the data is still essentially a disjointed set of separate analyses over a TREF run.

Thus, prior to the present invention, analytical temperature rising elution fractionation and high temperature continuous viscometry have not been utilized as a means for evaluating polymers.

SUMMARY OF THE INVENTION

The development of the system of the present invention combines the two analytical tools—ATREF and continuous viscometry—and fulfills the recognized need for concurrent molecular weight data for fractions of a polymer obtained as a function of its crystallinity (or density or branching number).

Initial efforts were confounded by the high temperature requirements of the system. Since ATREF relies upon the solubility of various polymer crystalline fractions at the melting point of the fraction, and crystalline polymers have fractions with melting points well in excess of 100° C., a viscometry system capable of providing continuous data at high temperatures is required.

The present invention represents the culmination of these efforts. The invention comprises a method for fractionating crystalline and semicrystalline polymers as a function of branching utilizing analytical temperature rising elution fractionation (ATREF) and determining, continuously, the instantaneous specific viscosity Spv and instantaneous concentration c of the continuously eluting stream, by taking progressive readings with instrumentation designed to determine the instantaneous specific viscosity and instantaneous concentration.

This latter analysis is possible because the eluate is subsequently passed through a high temperature viscometer and a mass detector, and the data collected therefrom is utilized to determine the instantaneous intrinsic viscosity Intv, which can be used to determine the instantaneous viscosity average molecular weight $Mv_i$ or the various fractions.

The invention, operating in the "foreground" processing mode, is capable of acquiring and storing raw mass detector data Wdata and differential pressure data Dp from one fractionation of a polymer sample, while analyzing similar data in the "background" mode from the fractionation of another polymer sample. In the background mode, this stored data can be analyzed electronically to produce data, such as instantaneous specific viscosity Spv data, instantaneous concentration c data, instantaneous intrinsic viscosity Intv data, and instantaneous viscosity average molecular weight data $Mv_i$ of the various fractions. The data can be displayed in written form or used to produce chart displays. It also can be used for subsequent analysis.

More particularly, the invention resides in a method for analyzing such a polymer sample solution comprising the steps of: (a) precipitating the polymer sample solution over a cooling temperature gradient to produce a precipitated polymer sample, said precipitated polymer sample being precipitated as a function of its crystallinity or branching configuration or density; (b) eluting said precipitated polymer sample over a heating temperature gradient to produce successive fractions of a fractionated polymer sample solution; (c) successively measuring the instantaneous concentration of the successive fractions of said fractionated polymer sample solution, at a first temperature in excess of a precipitation temperature of said fractionated polymer sample solution, to produce instantaneous concentration c data; and (d) successively measuring the instantaneous specific viscosity of the successive fractions of said fractionated polymer sample solution, at a second temperature in excess of a precipitation temperature of said fractionated polymer sample solution, to produce instantaneous specific viscosity Spv data; and (e) determining the instantaneous intrinsic viscosity Intv of the successive fractions of said fractionated polymer sample solution in accordance with said instantaneous concentration c data from step (c) and said instantaneous specific viscosity Spv data from step (d).

The invention also resides in an apparatus for analyzing such a polymer sample comprising; (a) means for precipitating the polymer sample solution over a cooling temperature gradient to produce a precipitated polymer sample, said precipitated polymer sample being precipitated as a function of its crystallinity or branching configuration or density; (b) means for eluting said precipitated polymer sample over a heating temperature gradient to produce successive fractions of a fractionated polymer sample solution; (c) first means for successively measuring the instantaneous concentration of the successive fractions of said fractionated polymer sample solution, at a first temperature in excess of a precipitation temperature of said fractionated polymer sample solution, to produce instantaneous concentration c data; (d) second means for successively measuring the instantaneous specific viscosity of the successive fractions of said fractionated polymer sample solution, at a temperature in excess of a precipitation temperature of said fractionated polymer sample solution, to produce instantaneous specific viscosity Spv data; and (e) third means for determining the instantaneous intrinsic viscosity Intv of the successive fractions of said fractionated polymer sample solution in accordance with said instantaneous concentration data c from said first means and said instantaneous specific viscosity data Intv from said second means.

BRIEF DESCRIPTION OF THE DRAWINGS

FIGS. 4A and 4B are side views of ATREF columns of the present invention.

FIG. 5 is a schematic representation of a typical viscometer within the scope of the present invention.

DETAILED DESCRIPTION OF THE INVENTION

Table of Contents

SECTION

I. SYSTEM DESIGN
II. SYSTEM OPERATION
III. THEORY AND IMPLEMENTATION OF ON-LINE MOLECULAR WEIGHT CALIBRATION AND ANALYSIS BY CONTINUOUS VISCOSITY COUPLED WITH ANALYTICAL TEMPERATURE RISING ELUTION FRACTIONATION
A. Necessary Assumptions for the Analysis
IV. DATA COLLECTION AND MANIPULATION
V. EXAMPLES
Example 1
Example 2
Example 3
Example 4
Example 5
Example 6
Example 7

The system of the present invention, analytical temperature rising elution fractionation coupled with continuous viscometry, is most easily described in terms of its three major components. These are (1) the solvent pumping system, (2) the column, temperature bath and circulator/temperature controller, and (3) the detection system and data accumulation and development system. Each of these major components will be described in turn, as well as a description of the initial operation of the system.

I. SYSTEM DESIGN

Figures 1, 2, 3:
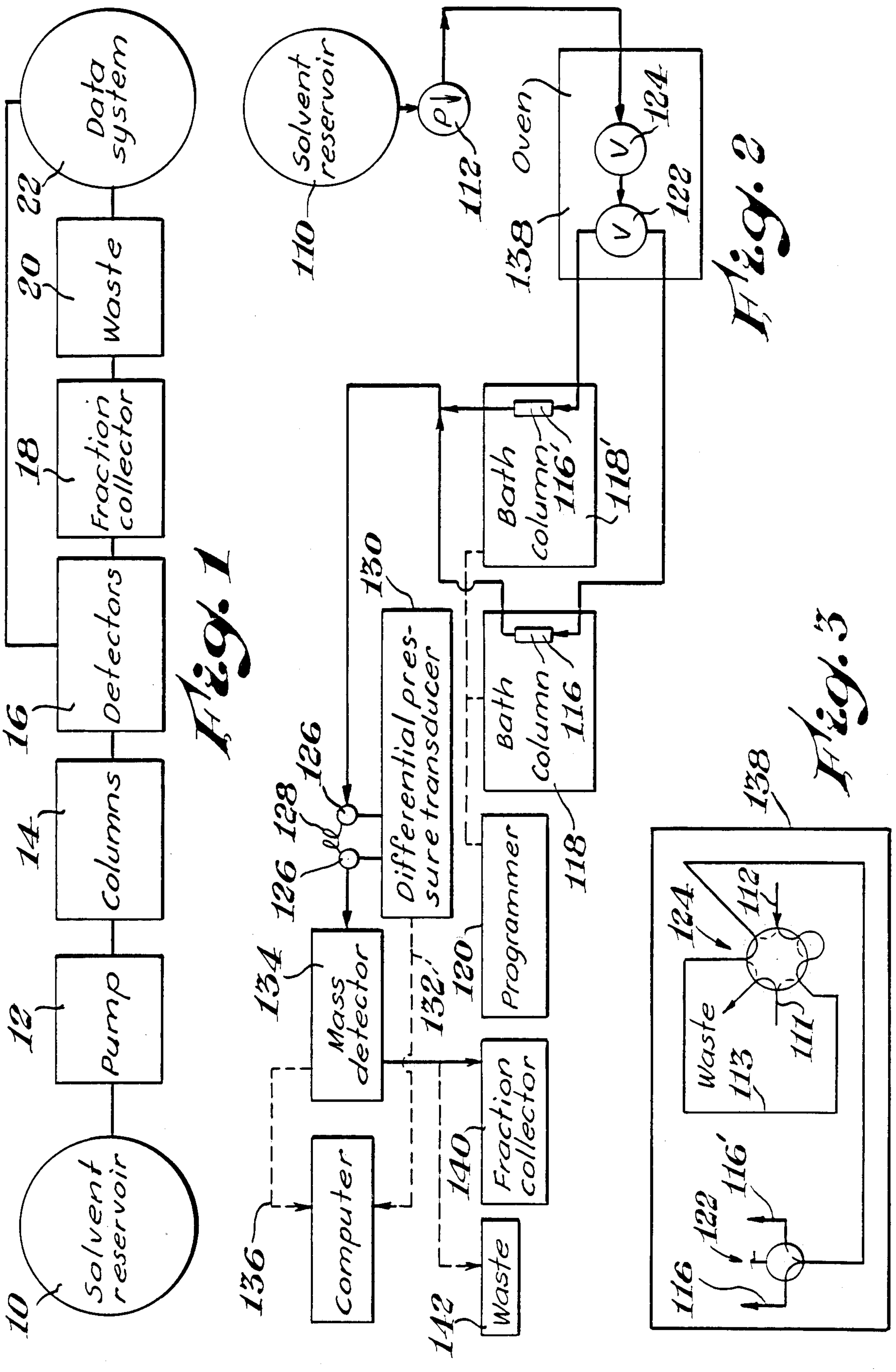
FIG. 1 is a schematic representation of the system, in block diagram form.
FIG. 2 is a schematic, in block diagram form, of the system in greater detail.
FIG. 3 is an exploded view of valves 122 and 124.

FIG. 1 is a schematic representation of the system, in block diagram form. Referring to FIG. 1, reference numeral 10 is a solvent reservoir; 12 is a solvent pump; 14 is a fractionation column, temperature bath, and controller/circulator; 16 is a detection system for detecting both concentration (mass) and viscosity; 18 is a fraction collector (optional); 20 is a waste collection system; and 22 is a data acquisition and processing system.

FIG. 2 is a schematic, in block diagram form, of the system in greater detail. Referring to FIG. 2, reference numeral 110 is a solvent reservoir; 112 is a solvent pump; 116 and 116' are fractionation columns, piped for alternate use in the system; 118 and 118' are oil baths; 120 is a temperature programmer; 122 is a two-position four-port valve (shown in greater detail in FIG. 3); and 124 is a two-position eight-port valve (shown in greater detail in FIG. 3). The valve 124 is used only during mass detector calibration.

The detection system is shown in FIG. 2 as the even numbers 126–136. In one embodiment shown in FIG. 2, the viscosity detector is represented by the even numbers 126–132. Reference numeral 126 denotes two zero-dead-volume "Tees"; 128 is a capillary tube; 130 is a differential pressure transducer; and dashed line 132 transmits the electrical signal from 130 to the data collection system (not shown). Reference number 134 represents the mass detector, with dashed line 136 representing the electrical signal output to the data collection system (not shown). Reference numberal 138 is an oven for maintaining valves 122 and 124 at elevated temperature.

Referring to FIG. 3, an exploded view of valves 122 and 124, as well as oven 138, is shown. It may be seen that valve 122, a two-position, four-port valve, permits solution and/or sample to pass into either column 116 or 116'. Similarly, valve 124, a two-position, eight-port valve, permits the calibration solution to be introduced into the system from a syringe connected to a port 111 (position shown with solid lines); into the sample loop 113, and then (position shown in dotted lines) into the two-position, four-port valve 122 for introduction into the selected column.

The solvent (mobile phase) reservoir (10 of FIG. 1 and 110 of FIG. 2) is typically made of stainless steel or glass, but must be inert to the mobile phase and not be easily broken. For convenience, some reservoirs are designed so that the mobile phase may be degassed in situ to prevent bubbles from forming in the detector during the separation. To facilitate in situ degassing, reservoirs may be equipped with a heater, a stirring mechanism (e.g., magnetic stirring bar), and separate inlets for vacuum or nitrogen purge. Degassing may be achieved by applying a vacuum to the filled reservoir for a few minutes with stirring, or by thoroughly purging the mobile phase with helium, which has a very low solubility in virtually all liquids. A helium or nitrogen purge also prevents oxygen from redissolving in a sensitive mobile phase after degassing, and in some instances, improves safety by preventing accidental ignition of flammable vapors. Mobile phase reservoirs are discussed in detail by Yau, W. W. et al., *Modern Size-Exclusion Liquid Chromatography,* pp 126–128 (1979), John Wiley & Sons, Inc.

The solvent pump (solvent metering system) is essentially that used in conventional gel permeation chromatography operations. Typically, these pumps provide a constant, reproducible supply of mobile phase to the column, with relatively high pump pressures required to overcome resistance to flow offered by the small particles used in the columns. Most modern solvent metering systems for chromatography are constructed of stainless steel and Teflon ® for a maximum of resistance to chemical attack. Pump seals made from virgin or filled Teflon ® resist all solvents that have been used for gel permeation chromatography (GPC), including concentrated sulfuric acid. Two general types of solvent-metering systems are available: positive-feed and flow-feedback systems, both with and without compressibility and pulsation compensation. Commercially available pumps may be classified into three groups; reciprocating, positive displacement and constant pressure Typical commercially available pumps suitable for the practice of the present invention include the Waters 6000 series by Waters Associates of Millipore and all others preferably possessing constant flow to approximately ±1 percent and no pulse, or low pulse performance.

®Trademark for tetrafluoroethylene fluorocarbon polymers.

A first column design is shown in FIG. 4A. This column is 2.5 cm in diameter by 12.5 cm in length and comprises a stainless steel pipe with steel plates welded to the ends as caps. These end caps are capped with 0.6 cm pipe threads and the appropriate Swagelock ® fittings used to couple them to 0.3 cm, large ID stainless tubing. The columns are loaded with cylindrical steel shot, typically 0.57×0.57 mm obtained from Pellets, Inc. (Tonawanda, N.Y.).

The caps are fitted with a fine mesh wire gauze to retain the shot under flow. Referring to FIG. 4A, the column 210 is shown immersed in an oil bath 222. The column 210 is filled with the shot 212. The lines in FIG. 4A are used, respectively, for manually filling the column 210 with hot polymer solution (214), overflow (218), solvent uptake from the pump (216), and an exit to the detectors (220). The operation of this column is described in more detail below.

This early column design was further improved by reducing the size even more as depicted in FIG. 4B. These two designs will be referred to as large and small columns, respectively. The small column (243) consists of 7.5×0.9 cm stainless steel tubing fitted with 0.9 cm to 0.15 cm Swagelock ® reducing unions (241 and 242) and packed with the same size steel shot. The interstitial volumes of the two columns are 27 and 1.5 cm respectively.

In the early work, where it was important to obtain separate fractions for subsequent SEC analysis, the larger columns were necessary. However, as knowledge of the power of this technique accumulated, it became increasingly desirable to reduce the column size further, to optimize column separation and decrease analysis times. This reduction in size was achieved at the expense of the ability to collect fractions, a primary motivation for establishing a new technique for molecular weight determination.

The oil bath 222 typically comprises a container built from 0.3 cm thick steel plate and accommodating a temperature controller/circulator, typically a Haake N3 temperature controller/circulator. In one embodiment, approximately 30 liters of heating oil are used to bring the level up to 17.5 cm so that the column and its end cap fittings are fully submerged. The bath is programmed to linearly change the temperature between 25° C. and 130° C. during normal operation. The bath itself is fitted with two permanent Swagelok ® unions for solvent connections to the rest of the system. This simplifies the column change-out procedure.

In order to evaluate the various fractions eluting from the fractionating column, it is necessary to measure both the viscosity and the concentration of the eluting polymer solutions at the same point. Solution viscosity may be accurately measured using devices similar to that of A. C. Ouano, *J. Poly. Sci.* A1, 9:2179 (1971), which derived an output signal based on the pressure drop across a capillary of known dimensions. In the Ouano device, the effluent stream enters the capillary which is configured in parallel with a differential pressure transducer and serves as a flow restriction. The volume of the capillary determines the cell volume and the magnitude of the pressure drop as measured by the transducer for a given fluid system.

For constant Poiseuille-type flow, that is laminar flow through capillaries, the pressure drop is directly proportional to the viscosity of the fluid, as follows:

$$\Delta P = k\eta$$

where the instrumental constant k equals $(8/\eta)Q(L/R^4)$. (The instrumental constant k depends on the flow rate (Q), the capillary length (L) and the capillary radius (R)).

Consequently, at constant flow rate and for a particular capillary, the ratio of the pressure drop of the sample stream to that of the pure mobile phase ($\Delta P_1/\Delta P_0$) is equal to the ratio of the viscosity of the sample stream to the viscosity of the mobile phase, ($\eta_1/\eta_0$). Since the concentration, c, of the sample can be obtained from the mass detector (that is, a differential refractometer), the instrinsic viscosity [η] can be calculated from either of the following formulas:

$$\lim_{c \to 0} \ln\left(\frac{\Delta P_1}{\Delta P_0}\right)/c = \eta \text{ or}$$

$$\lim_{c \to 0} \frac{1}{c} \frac{\Delta P_1}{\Delta P_0} - 1 = \lim_{c \to 0} \frac{1}{c} \frac{\Delta P_1 - \Delta P_0}{\Delta P_0} =$$

-continued $$\lim_{c \to 0} \frac{1}{c} \frac{\Delta P'}{\Delta P_0} = \eta$$

where $\Delta P_0$ and $\Delta P_1$ are the pressure drops due to the pure mobile phase and the sample solution respectively, and $\Delta P'$ is $\Delta P_1 - \Delta P_0$ or the difference in solvent and solution pressure drops.

Thus, if the pressure transducer produces a linear voltage response, v, then the change in the response, $\Delta v$, is proportional to the difference between the pressure drop across the capillary of the solution containing polymer and the pressure drop across the capillary of pure solvent. The zero point of v is set such that at zero pressure (no flow) v is zero: consequently, $\Delta P_0$, the magnitude of the pressure drop due to pure solvent, should produce some proportionately constant response, $v_s$. The magnitude of v normally is very nearly equal to $v_s$ so that electronic "bucking" and amplification are necessary to detect the difference in voltage $\Delta v$. Accordingly, specific viscosity as a measure of change in voltage of the differential pressure transducer is expressed as follows:

$$\eta_{sp} = \frac{v}{v_s} - 1 = \frac{v - v_s}{v_s} = \frac{\Delta v}{v_s}$$

In another embodiment, the viscosity may be measured using a device as disclosed in U.S. Pat. No. 4,463,598 to Max A. Haney. A schematic diagram of this instrument, which is commercially available from Viscotek of Porter, Tex., is shown in FIG. 5. As shown in FIG. 5, it comprises four matched capillaries and two differential pressure cells. This "Wheatstone bridge" design has the advantage of measuring the solvent viscosity and solution viscosity simultaneously. This instrument is more sensitive and has a superior signal to noise ratio than the simpler single capillaries.

Similarly, low-angle laser light-scattering (LALLS) photometry has been used to monitor effluents. See Yau et al. (supra), pp. 156–164. A commercially available apparatus built by Chromatix, a subsidiary of Milton Roy Company, is capable of operation at these concentration ranges and range of weight average molecular weights. See "Measurement of the Absolute Molecular Weight and Molecular Weight Distribution of Polyolefins," *Chromatix Appl. Note* LS-3, 1978.

The concentration detector may be any suitable device such as a photoelectric colorimeter or a refractometer, for measuring relative changes in the concentration of the solution. A differential refractometer represents one embodiment for use in the present invention and comprises a combination of optical, mechanical and electrical components. Differential refractometers are probably the most widely used detectors for use in gel permeation chromatography analysis. The device continuously measures the difference in refractive index (DRI) between the mobile phase consisting of pure solvent and the mobile phase consisting of polymer dissolved in pure solvent. Differential refractometers are described in greater depth in Yau et al., supra, pp. 148–156; U.S. Pat. No. 3,458,437 to Ouano; and U.S. Pat. No. 3,674,373 to Waters et al. Suitable mass detectors include, but are not limited to, the Waters 401 DRI, the Waters high temperature DRI (as embodied in the Waters 150C ALC/GPC instrument), and a Wilkes single beam infrared detector.

The data collection system of this invention comprises suitable electronics for converting the analog signals received from the measurement devices into corresponding digital data words or values. A wide variety of conventional devices may be used.

The inventors have found that it is advantageous to utilize a buffer amplifier disposed between the detectors and the analog to digital converter. Any suitable type of buffer amplifier can be employed. The gain of the buffer amplifier is selected to produce an output signal of a desired amplitude range for a given input signal of the amplitude range provided by the associated detector. Representative of a suitable buffer amplifier is that made by Batel under Model No. AM-435. It should be understood that any suitable type of buffer amplifier can be employed, as well as numerous "gate" cards with program selectable attenuations.

The output from the buffer amplifier is converted into a corresponding digital data word. Any suitable type of analog-to-digital (A/D) converter can be used. The computer system (not shown) of the present invention interrogates the A/D converter so that it will provide the desired sampling of the analog signal at a given point in time. In this way, the computer system of the present invention can sample the input signals at preselected times during the fractionation of the polymer sample. It will be appreciated that these precise time measurements are extremely important in correlating the sampled data with the particular polymer fraction being analyzed by the present invention.

Described below with reference to FIGS. 17A to 21B are representative software programs used by the present invention to provide the analysis of the data obtained during the fractionation of the polymer sample. These programs allow the present invention to both accumulate data (raw mass detector data Wdata and differential pressure data Dp) from an ongoing experiment ("foreground" processing) and to analyze it subsequently ("background" processing) to produce data, such as instantaneous specific viscosity Spv data, instantaneous concentration c data, instantaneous intrinsic viscosity Intv data, and instantaneous viscosity average molecular weight data $Mv_i$ of the various fractions. This data can be displayed in written form or used to produce chart displays. It can also be used for subsequent analysis.

II. SYSTEM OPERATION

In the following discussion, the parameters in the text are for the large column previously discussed, while those in brackets are those used for small columns.

The two major areas of operation necessary for analytical temperature rising elution fractionation are (1) the cool-down or precipitation step and (2) the warm-up or elution step, which steps are implemented in that order. The sample must be deposited in a column in advance before analysis can begin. Analytical temperature rising elution fractionation utilizes the physical properties of crystallinity to differentially precipitate polymer in an adequately designed column. Polymer sample solution containing, for example, 0.5 gm of polymer in 50 cc of solvent (typically 1,2,4-trichlorobenzene (TCB)) at 135° C., is added to the column in an oil bath at 135° C. Alternative polymer sample solutions are defined here to include substitution of other solvents or even molten polymers with no solvent. An 0.3 cm stainless tube is connected to one end of the column and placed in a reservoir of TCB. The other end of the column is plugged. Then, as the column is cooled from 135° C. to ambient temperature at 0.04° C./min. [0.17° C./min.], TCB from the reservoir will be pulled into the column (instead of air) as the TCB polymer solution contracts upon cooling. Precipitation of various fractions occurs as the temperature drops below the precipitation point for that fraction. Thus, at ambient temperature, the entire polymer content of the column has been fractionated (preferentially precipitated) in accordance with the branching characteristics (crystallinity) of the individual fractions.

After the column has reached ambient temperature, analysis of the various fractions begins. Each column is placed in an oil bath as shown in FIG. 2. The column is purged with TCB at ambient temperature for 20 to 30 minutes at a flow rate of 2.5 ml/min [1.0 ml/min]. The oil bath is programmably heated at 0.2° C./min [0.8° C./min] to 130° C. with the flow rate maintained at 2.5 ml/min [1.0 ml/min]. The concentration of polymer in the TCB stream eluting from the column changes as a function of both temperature and crystallinity. These changes may be measured, for example, by use of a differential refractometer. Further, before the polymer solution reaches the differential refractometer, it goes through a viscometric detector, which typically is a detector which measures viscosity as a function of pressure drop across a capillary tube.

Data acquisition and analysis are done automatically, typically utilizing a Hewlett-Packard (HP) 9845B desktop computer and HP6940B Multiprogrammer and HP9872C Plotter or equivalents thereof under control of the computer programs described below with references to FIGS. 17–21A. Any suitable hardware and/or software can be used in the present invention to analyze the data from the fractionated polymers to produce the desired output data, such as instantaneous intrinsic viscosity Intv data and the instantaneous viscosity average molecular weight data $Mv_i$ of the various fractions.

Referring to FIG. 4A, operation of the system is as follows. The column is full of clean solvent from a previous fractionation, or is filled by manual injection if this is the first fractionation for that column. A 50 cc syringe, previously heated in an oven to the same temperature, is connected to a Luer lock fitting which has a 10 cm piece of 0.3 cm stainless steel tubing soldered in place of a needle. At the opposite end of the tubing, a Swagelock ® fitting is used to attach the syringe assembly to the column by line 214. Lines 216 and 220 are kept closed during the filling procedure. All 50 cc's of the polymer solution are injected into the column, and the overflow is collected in a bottle at line 21. The interstitial volume of the column is established from the weight difference of the TCB full and TCB empty columns divided by the density of ambient TCB to yield approximately 27 cc [1.5 cc].

In one embodiment, a rack may be constructed to accommodate the simultaneous cooling of six columns. The overflow tubes are long enough to reach outside the bath to a test tube rack containing six test tubes of fresh TCB with the ends positioned near the bottom of each respective tube. This last arrangement prevents the intake of air once the columns are cooled.

The bath is then programmably cooled at −0.04° C./min [−0.17° C./min] from 130° C. to near 30° C. At this point, the circulator is turned off, and the columns are allowed to cool off to room temperature (approximately 25° C.). The whole cooldown step requires nearly three days [10 hrs].

The column or columns are now ready for the elution step. Referring again to FIG. 4A, a smaller single column rack is used to position the column in the bath. Line 216 connects column 210 to the pump (not shown), and line 220 connects it to the differential refractometer or other concentration measurement device. Line 214 and 218 are capped. The pump is set to deliver 2.5 cc/min [1.0 cc/min]. The detectors are zeroed. Normally, the zero position on the recorder is arbitrarily chosen to be 10 percent of full scale to allow for base line drift. When the base line is stable and in the desired position, the four-way valve is rotated 90° to connect the column to the rest of the system. The initial bath temperature is generally between 25° C. and 30° C., and is noted on the recorder.

Within the first five minutes of a run, an intense positive pen deflection on the chart recorder occurs due to DRI response, lasting as much as 1.5 hours [30 to 45 minutes], before a baseline condition is reestablished. The cause of this strong initial response from the refractometer is not completely understood, but experiments performed using columns containing no precipitated polymer have also shown the same behavior. Consequently, the strong signal provided by the refractometer during the initial stages of an actual fractionation is not due entirely to eluted polymer. While this initial peak is eluting, the bath is left at its initial temperature. When the pen recording the refractometer response returns to a baseline condition, the temperature programmer (and if large columns are used, the fraction collector) is started. This reestablished baseline is often different from the initial baseline, due to slight changes in pressure when the column is included in the system and possibly due to drift in the electronics, although the initial and reestablished base lines are usually within 5 percent of full scale of one another. The program temperature increase is set to 0.2° C./min [0.8° C./min] and ramps up to 100° C. above the initial temperature. (If used, the fraction collector receives the eluant at 20 minute intervals, amounting to about 50 cc total volume.) The system operation from this point is essentially unattended. The entire elution step of the fractionation requires from 8 to 10 hours [1 to 2 hours]. When the bath temperature reaches 110° C., virtually all of the polymer has eluted and the refractometer response returns to the baseline value.

III. THEORY AND IMPLEMENTATION OF ON-LINE MOLECULAR WEIGHT CALIBRATION AND ANALYSIS BY CONTINUOUS VISCOSITY COUPLED WITH ANALYTICAL TEMPERATURE RISING ELUTION FRACTIONATION

A. Necessary Assumptions for the Analysis

ATREF analysis provides a weight percent distribution of semicrystalline polymers, which is a function of their short chin branching (SCB). This is derived from the elution temperature for a given fraction. Weight percent measurements are achieved through the use of a differential refractometer or an infrared absorbance at 3.47 (carbon-hydrogen stretch).

Narrow molecular weight fractions of linear polyethylene have a distinct relationship between molecular weight (M) and intrinsic viscosity ([η]). This relationship is stated below:

$$[\eta]=KM^{a} \quad (1)$$

The above equation (1) is known as the Mark-Houwink-Sakurada relationship, and is applicable to solutions of linear polymers. The values of the constants, K and a, are tabulated for a variety of solvents, temperatures, and polymer systems (Kurata, M. et al. *Polymer Handbook.* J. Brandurp and E. H. Immergut, Ed., Chapt. IV-1, Interscience, New York, 1966). The values for polyethylene for K and a used in the present invention were obtained by Moore (1972) in unpublished work, and compare very favorably with the published results of Ram and Miltz (A. Ram and J. Miltz, *J. Appl. Polym. Sci.* Vol. 15, p. 2369, 1971). The entries below compare Moore's results for polyethylene to those of Ram and Miltz.

| | K | a |
|---|---|---|
| Moore | $6.23\ 10^{-4}\ \frac{dl}{g}$ | 0.695 |
| Ram and Miltz | $5.96\ 10^{-4}\ \frac{dl}{g}$ | 0.7 |

Solvent viscosity may be accurately measured using devices similar to that of Ouano (supra) which utilizes the pressure drop ΔP across a capillary of known dimensions, as follows:

$$\Delta P = \frac{8QL}{R^4}\eta_0 \quad (2)$$

$$\Delta P = k\eta_0 \quad (3)$$

where

ΔP equals the pressure drop across a capillary;

k equals $8QL/\pi R^4$

Q equals flow rate

L equals the length of the capillary;

R equals the radius of the capillary;

$\eta_0$ equals the viscosity of pure solvent; and the relative viscosities $\eta_{rel}$ are expressed as the ratio of the pressure drop:

$$\eta_{rel} = \frac{\Delta P}{\Delta P_0}$$

where ΔP is the pressure drop of the solution and $\Delta P_0$ is the pressure drop of pure solvent, and the specific viscosity, sp, is the ratio minus one:

$$\frac{k \cdot \Delta P}{k \cdot \Delta P_0} - 1 = \frac{\Delta P - \Delta P_0}{\Delta P_0} = \eta_{sp} \quad (4)$$

Thus, if the pressure transducer in response to a change in pressure ΔP produces a linear voltage change with respect to an initial response, v, then the change Δv in the response is given by the numerator:

$$\Delta v \propto \Delta P - \Delta P_0 \quad (5a)$$

The denominator may be calculated by setting v at zero pressure (no flow) to zero so that $\Delta P_0$ is proportional to $v_s$, the response of pure solvent. Normally, $v_s+\Delta v$ is very close to $v_s$, so electronic "bucking" and amplification to detect and measure Δv accurately are necessary. Equation 4 above, expressed as voltage, is given below:

$$\eta_{sp} = \frac{v}{v_s} - 1 \quad (5b)$$

Alternatively, the viscosity may be measured using a device designed by Haney, supra. This instrument is more sensitive and has a signal to noise (S/N) ratio superior to that of the simpler single capillaries. The principle is outlined below, with reference to FIG. 5.

This unique "Wheatstone bridge" design has the advantage of measuring the solvent viscosity and solution viscosity simultaneously. As the solvent changes to solution with increasing solute concentration, an in-line reservoir 255 produces a time lag at $R_4$ (254) of FIG. 5. Provided this reservoir is sufficiently large, the liquid flowing through $R_4$ (254) will be pure solvent, while $R_1$ (251), $R_2$ (252), and $R_3$ (253) have nearly equal concentrations of solute flowing through them.

Haney ("A Differential Viscometer—Part Two," *American Laboratory,* 17(4) 1985) has derived the necessary relationships as shown below. ΔP is the pressure difference at any time as indicated by the transducer in the bridge 256. IP is the inlet pressure or the pressure drop across the whole bridge 257. The system can be analyzed by defining $P_i$ (where i is a positive integer from 1 to 4) as the pressure drop over capillary tube $R_i$ (see FIG. 5) so that the following equation applies:

$$\frac{\Delta P}{IP} = \frac{P_4 - P_3}{IP} \quad (6a)$$

Since identical solutions flow through resistances $R_1$ and $R_3$ at the same flow rate, IP equals $2P_3$, and equation (6a) becomes:

$$\frac{\Delta P}{IP} = \frac{P_4 - P_3}{2P_3} = \frac{1}{2}\ \frac{P_4}{P_3} - 1 \quad (6b)$$

Applying Poiseuille's law to $R_3$ and $R_4$:

$P_3=k_3\ \eta$; $P_4=K_4\eta_0$

Therefore: (because the capillaries are of equal dimension)

$$\frac{P_4}{P_3} = \frac{k_4\eta_0}{k_3\eta} = \frac{Q_4\eta_0}{Q_3\eta} \quad (6c)$$

where $Q_3$ equals the flow rate in $R_1$ and $R_3$;

$Q_4$ equals the flow rate in $R_2$ and $R_4$;

$\eta$ equals the viscosity of the solution; and $\eta_0$ equals the viscosity of pure solvent.

The ratio of flow rates $Q_3$ divided by $Q_4$ is equal to the inverse ratio of the combined resistance of the corresponding side of the bridge as indicated by the following equation:

$$\frac{Q_4}{Q_3} = \frac{\eta + \eta}{\eta + \eta_0} = \frac{2\eta}{\eta + \eta_0} \quad (6d)$$

Combining equations 6b, 6c and 6d yields the following equation:

$$\frac{\Delta P}{IP} = \frac{1}{2}\ \frac{\eta - \eta_0}{\eta + \eta_0} \quad (7a)$$

Substituting the previous definition for specific viscosity yields:

$$\frac{\Delta P}{IP} = \frac{\eta_{sp}}{2\eta_{sp} + 4} \quad (7b)$$

This equation after rearrangement gives the following useful relationship:

$$\eta_{sp} = \frac{4\Delta P}{IP - 2\Delta P} \quad (7c)$$

The values WP and IP are output respectively as v, a 10 mv signal, and as vI, a 1 volt signal. The attenuation of v is variable between 20 and 5000 pascals, while vI is fixed at 100 Kpascals full scale.

v/10×instrument attenuation=WP in pascals vI×100=IP in K pascals

Since data is sampled digitally on a typical A/D board, there are additional attenuation factors to be considered so that the numbers used can be related back to Equation 7c. To allow for generalization, the values v and vI will be used to represent those A/D data, although it shall be understood that proportionality constants exist. Thus, a more general set of equations are as follows:

$v\,F_1 = \Delta P$ $vIF_2 = IP$

Where $F_1$ and $F_2$ are overall attenuation factors which convert the digital data to the corresponding pressure units. $F_1$ is the differential pressure attenuation factor, and $F_2vI$ is the inlet pressure in pascals. Equation 7c may now be written in a more useful form, as follows:

$$\eta_{sp} = \frac{4F_1v}{F_2vI - 2F_1v} \quad (7d)$$

Since the change in inlet pressure as reflecting in the value of $F_2vI$ in small, this product will be considered a constant and a single initial value suffices.

Using either method to obtain the specific viscosity, the intrinsic viscosity can be accurately estimated as follows by assuming that the observed instantaneous concentration, c, is dilute enough to be close to the extrapolated value:

$$[n] \simeq \frac{\eta_{sp}}{c} \quad (8)$$

With ATREF, it is not correct to use the concentration of the initial solution, so the detector itself is calibrated against a known standard. A working calibration is obtained by least squares best fit of the instantaneous concentration, c, versus mass detector response, r. (Again, it is understood that r is a digital number.)

$$r = m'c + b' \quad (9)$$

where c is in g/100 ml=g/dl

A more useful version of equation 9 is expressed in equation 10a:

$$c = \frac{r}{m'} - \frac{b'}{m'} \quad (10a)$$

$$-\frac{b'}{m'} = b,\ \frac{1}{m'} = m$$

$$c = mr + b$$

where m' and b' are the least square slope and intercept, respectively, for response versus concentration. The corresponding values of m and b describe the reverse relation of concentration versus response. Example 6 demonstrates the method for obtaining m' and b'.

Typical correlation coefficients for equation 9 range upwards from 0.998 for infrared detection at 3.46 m.

Concentrations range from $2.4\times10^{-2}$ to $1\times10^{-1}$, g/dl.

The same principles may be applied to any linear mass detection system (i.e., differential refractometer).

The judicious application of equation 10a to the following numerical method will provide instantaneous concentration data c.

In practice, the knowledge of the instantaneous concentration of the viscometer contents is more problematic than equations 9 and 10 would indicate. The difficulty arises because it is not possible to accurately determine the initial concentration in ATREF and instrument spreading will decrease the initial concentration of a standard solution by varying amounts depending upon how close to the column (in terms of dead volume) the detector resides. The most problematic effect is primarily a result of diffusion. The actual concentration will be less than that which one might initially choose to inject. It is therefore necessary to integrate the signal response from the mass detector and calculate mean heights (or responses) $r_i$ from equation 10b for incremental areas.

$$r_i = \int_{t_i}^{t_i+1} f(t)dt/t_{i+1} - t_i\,dt \quad (10b)$$

(from the mean value theorem of integral calculus).

In equation 10b, the instantaneous mass detection response is described by the function f(t), where t is the elapsed time in minutes. The boundaries of the integration are arbitrary, but for convenience, they shall be those values of t for which the computer has measured the instantaneous value of f(t). Thus, $t_{i+1}-t_i$ is the sampling interval or 1.25 min. Assuming 1 cc/min, $t_{i+1}-t_i$ is the volume in milliliters or the elapsed time minutes bounding any two mass detector responses $f(t_{i+1})$ and $f(t_i)$. The magnitude of $\bar{r}_i$ will be approximated by a trapezoid since the change in signal between measurements is slow, as depicted in equation 10c, as follows:

$$\bar{r}_i = (f(t_i) + (f(t_{i+1}))/2\cdot(1.25) \quad (10c)$$

For a chromatogram consisting of n measurements, the total area, A, is given by equation 10d, as follows:

$$A = \sum_{i=1}^{n} \bar{r}_i = \frac{n}{2.5} \sum_{i=1}^{n} (f(t_i) + f(t_{i+1})) \quad (10d)$$

To find the average concentration of element i, $\bar{c}_i$, it will be assumed that the proportion of the total area A given by $\bar{r}_i$ will be equal to the same proportion of the total polymer injected. Thus, we are assuming a linear response. The total weight of injected polymer that flows through the system can be obtained from the volume of the injection, $V_o$, and the initial concentration $c_o$. By noting the flow rate, Q, the average concentration, $c_i$, for the $i^{th}$ element is given in equation 10e, as follows:

$$\bar{c}_i = c_o \cdot V_o \cdot Q^{-1} \cdot A^{-1} \cdot \bar{r}_i + b \qquad (10e)$$

where b is a concentration corresponding to the limit of detection.

Equation 10e indicates that $c_i$ and $r_i$ will have a linear relationship, just as was implied in equations 9 and 10a. The strategy then is to analyze known concentrations of polymer to arrive at the magnitudes of m and b in equation 9. An example of such a method utilizing linear regression analysis is included herein. Knowledge of the coefficients m and b in equation 10a allows the calculation of the instantaneous concentration c from a set of corrected mass detector responses $Rt_i$, by assuming that the average concentration $\bar{c}$ is very close to the instantaneous concentration c and that $Rt_i$ is very close to $\bar{r}_i$ to obtain equation 10a.

Equation 1 above is more commonly referred to as the Mark-Houwink-Sakarada (MHS) equation. Solving for M, and inserting the values for polyethylene, we obtain:

$$M = \left(\frac{[\eta]}{K}\right)^{1/a} = \left(\frac{[\eta]}{6.27 \times 10^{-4}}\right)^{1.44} = 40{,}900 \cdot [\eta]^{1.44} \qquad (11)$$

Remembering that $[\eta] \simeq \eta_{sp}/c$ (from equation 8) =

$$\eta_{sp} = \frac{4\Delta P}{P_i - 2\Delta P}$$

(from equation 7b) and $c - mRt_i + b$ (from equation 10a), equation 11 now becomes:

$$Mv_i = 40{,}900\left(\frac{4\ F_1\ Dp_i}{(F_2vI - 2F_1Dp_i)(mRt_i + b)}\right)^{1.44} \qquad (12)$$

where the variables are defined as the instantaneous viscosity average molecular weight $Mv_i$, the value corresponding to the pressure drop of the viscometer $Dp_i$, and the instantaneous mass detector response $Rt_i$ during a particular analysis. These latter values are read by the computer as described below.

From the definition of intrinsic viscosity, the following correction is applicable, for rigorous treatment of discontinuous measurements of the specific viscosity:

$$[\eta]\ \lim_{c \to 0} \frac{\eta_{sp}}{c} = \lim_{c \to 0} \frac{1}{c}\ \frac{\eta - \eta_o}{\eta_0} \qquad (12a)$$

From L'Hospital's Rule of limits, the above expression (12a) can be regarded as the following differential equation:

$$\lim_{c \to 0} \frac{1}{c}\ \frac{\eta - \eta_0}{\eta_0} = \frac{\eta - \eta_0}{\eta_0}\ \frac{d(c)}{dc} = \frac{1}{\eta_0}\ \frac{d\eta}{dc} \qquad (12b)$$

The data taken in the experiment for the instantaneous pressure drop is dp/dt, since it is acquired on a time basis. If k, is the proportionality constant of P to $\eta - \eta_o$, then the differential becomes:

$$\frac{1}{\eta_o}\ \frac{d\eta}{dc} = \frac{k}{P_0}\ \frac{d\eta}{dc} \qquad (12c)$$

The value of dP/dt, as indicated by the magnitude of the voltage change from the differential pressure cell is lim $\Delta P/\Delta t$ (thus the name differential pressure). To convert this to concentration, the chain rule of differentials is applicable.

$$\left(\frac{dP}{dt}\right)\left(\frac{dt}{dc}\right) = \frac{dP}{dc} \text{ and } \left(\frac{\Delta P}{\Delta t}\right)\left(\frac{\Delta t}{\Delta c}\right) = \frac{\Delta P}{\Delta c} \qquad (12d)$$

The value in parenthesis is just the raw differential data (pressure drop/1.25 min). These values are corrected slightly to approximate P/c.

Therefore, equation 12 becomes:

$$Mv_i = 40{,}900\left(\frac{4\ F_1\ Dp_i\ 1.25}{(F_2vI - 2F_1Dp_i)(mRt_i + b)}\right)^{1.44} \qquad (12e)$$

Equation 12e is the relationship that is employed to obtain the molecular weight. Since the molecular weights are derived from the MHS equation, they are viscosity average molecular weights defined mathematically as:

$$\bar{M}_{viscosity} = (\Sigma(w_i\ M_i)^a)^{1/a} \qquad (13)$$

where $w_i$ is the weight fraction having molecular weight $M_i$ and a is the exponent of the MHS equation. Therefore, the overall molecular weight distribution, as a function of elution temperature, is here expressed in terms of incremental viscosity average molecular weights. These increments are of fractions of the same crystallinity.

IV. Data Collection and Manipulation

Discussed below is representative hardware and software used to sample and store digital data values (such as raw mass detector data Wdata and differential pressure data Dp) of the polymer fractions that are sampled by the present invention. This stored digital data is then used in the "background" mode by certain analysis programs which provide the instantaneous specific viscosity Spv data, instantaneous concentration c data, instantaneous intrinsic viscosity Intv data, and instantaneous viscosity average molecular weight data $Mv_i$ of the various fractions of the polymer. Note that the hardware and the software discussed below are representative, and other types of hardware and software can be employed to implement the analysis of the present invention used to produce the desired output information.

A representative example of suitable computer hardware is an HP9845 microcomputer and an HP6940B Multiprogrammer fitted with process interrupt capabilities, a voltage monitor, a relay read back, and supporting software. The microcomputer and the multiprogrammer are made by Hewlett-Packard of Palo Alto, Calif. Such a microcomputer can utilize BASIC (HP Version 1) as its programming language. The electronics used to sample the analog signals from the detectors (raw mass detector data Wdata and differential pressure data DP) (see FIG. 2) indicative instantaneous Spv can also be of any suitable type that will convert the analog signals into suitable digital data signals or words. The software developed by the inventors emulates foreground/background processing, even though it is technically a single tasking device. However, the terms "foreground" and "background" will be used in the following discussion, because they are descriptive of the bifunctionality of the system.

Figure 17:
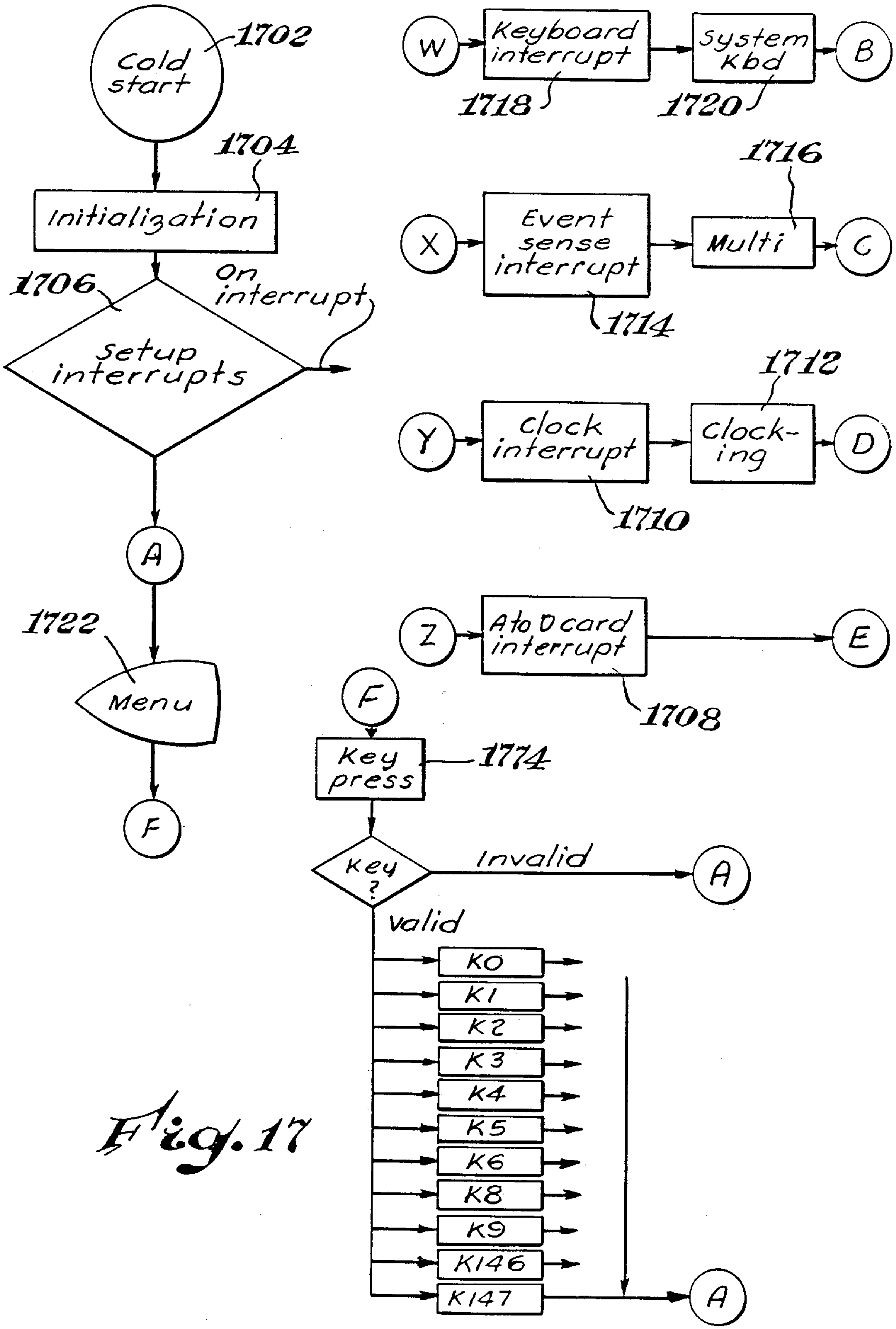
FIG. 17 is a flow chart of the various programs used in the invention to provide the foreground and background processing capability.

Referring now to FIG. 17, a flow chart of the representative programs of the present invention is shown. Turning first to the foreground/background processing emulation of one current embodiment of a data system for the present invention, data can be sampled and stored from one fractionation of a polymer sample while data from a previous fractionation of another polymer sample is being reduced to a meaningful format. Any suitable type of foreground/background processing capability can be used; optionally, single tasking reduction could be substituted if data reduction was not desired during data acquisition.

As shown in the flow chart of FIG. 17, the program starts with a cold start of the present invention, as shown by block 1702. Then, initialization of the main program is performed, as shown by block 1704. Thereafter, the interrupts W, X and Y are set up, as shown by decision block 1706. These interrupts W, X and Y allow the present invention to perform the background/foreground processing capability.

The interrupt having the highest priority is the Z interrupt. The Z interrupt allows the present invention to read data from the A/D card (not shown) as represented shown by block 1708. This data must be read in accordance with the clock of the present invention in order for the proper time correlation with sampled data to be present. In other words, because there is a constant flow rate, it is essential that the present invention know the time when a particular sample was taken in order to be able to perform the necessary analytical process discussed above with respect to the ATREF program discussed below.

The interrupt having the second highest priority is the interrupt Y. This interrupt is used in connection with the generation of the clock signals used to generate the timing of data sampling. When the clock interrupt is high, as indicated by block 1710, a clocking subroutine, either Clocking or Clocking 2, is called, as indicated by block 1712. These subroutines can be of any suitable type that allow the present invention to service the desired clock interrupts.

Figure 20:
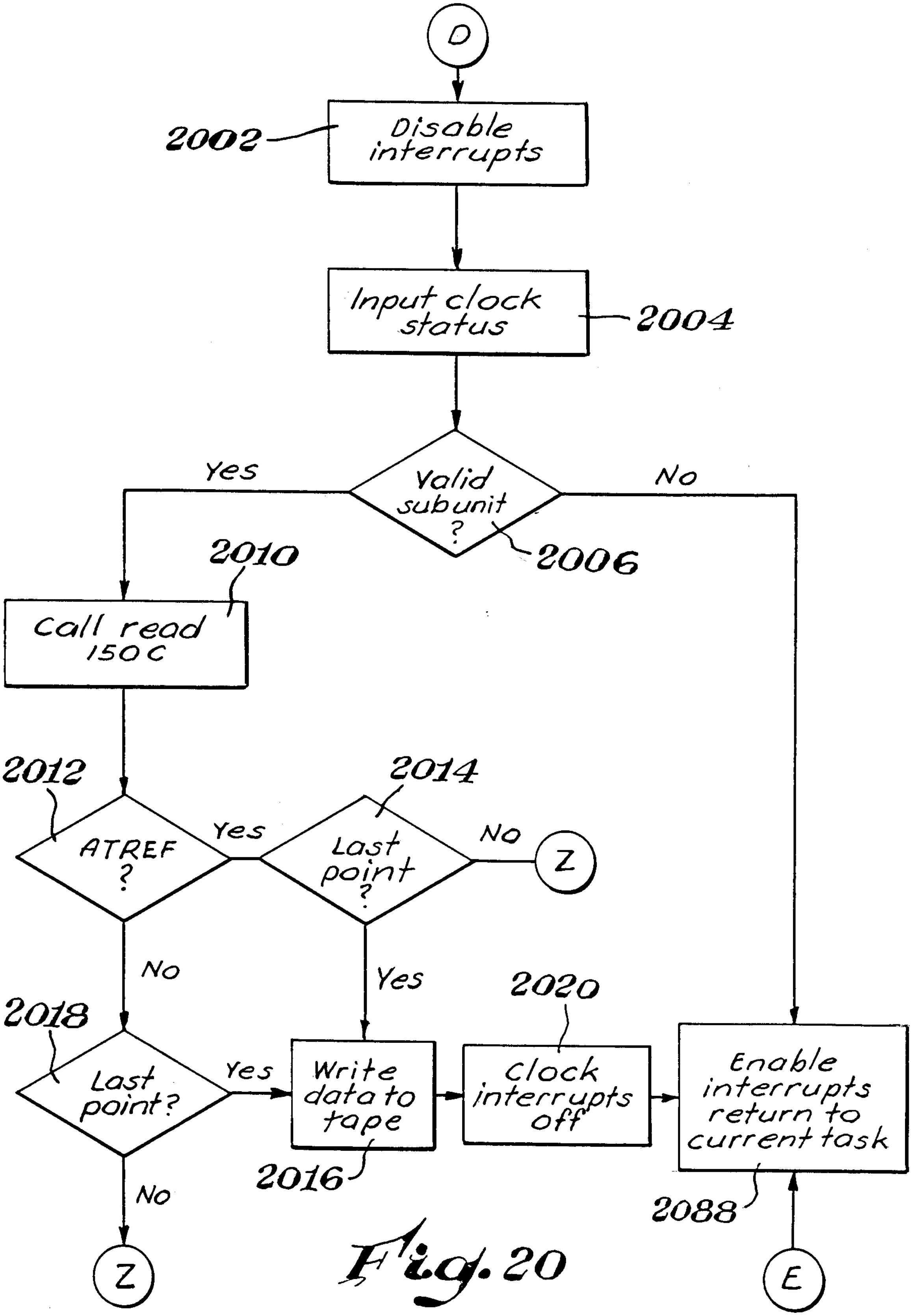
FIG. 20 is a flow chart of a representative computer program used to provide the clock interrupt.

FIG. 20 shows a flow chart of a representative program driven by a system clock to take voltage data at the proper times (block 1712). The interrupt is disabled, as indicated by block 2002, and the determination of which subunit has initiated the interrupt, as indicated by block 2004. A decision block 2006 then determined which clock number and subunit has initiated the interrupt. If an invalid clock number or subunit is detected, the program proceeds to re-enable the interrupt and return, which causes the program to return to its current task without any data acquisition occurring, as indicated by block 2008. However, after the decision block 2006 determines the valid clock number and subunit, the program then proceeds to read the data for a given polymer sample as indicated by block 2010. Since concurrent SEC analysis is likely, block 2012 is necessary to verify that ATREF data is being acquired. ATREF and SEC data are acquired at different sampling rates (SEC is 1 sample/15 sec. and ATREF is 1 sample/75 sec.).

Next, block 2012 determines whether all the data points have been obtained. If the answer is no, the program causes the subroutine to read the next sample using the FNRead system function at block 1708. In contrast, if the last ATREF point has been read, the data that has been obtained is written to a tape storage unit, as indicated by block 2016. An analogous test applies to SEC data if decision block 2018 determines that the last SEC point has been read. After the data has been written to the tape, the clock interrupts are turned off, as indicated by a block 2020. Thereafter, the program returns to its present task, as indicated by block 2008. In this way, the present invention allows the data being read during the fractionation of a polymer sample to be accurately correlated to the time at which it was read, concurrently with user interaction in background.

Referring now to the second to lowest priority interrupt, interrupt X, it is used to determine whether an external event has occurred within the present invention. By external event, it is meant that a particular occurrence has occurred in the present invention relating to its operation, as indicated by the change in state of a set of contact closures. When an event interrupt goes high, as indicated by block 1714, the event sense service routine program Multi is called up, as indicated by block 1716. The primary use of this "event sensing" routine is to inform the system that an analysis is beginning and to set up the clock interrupts by programming the real time clock(s).

Figure 19:
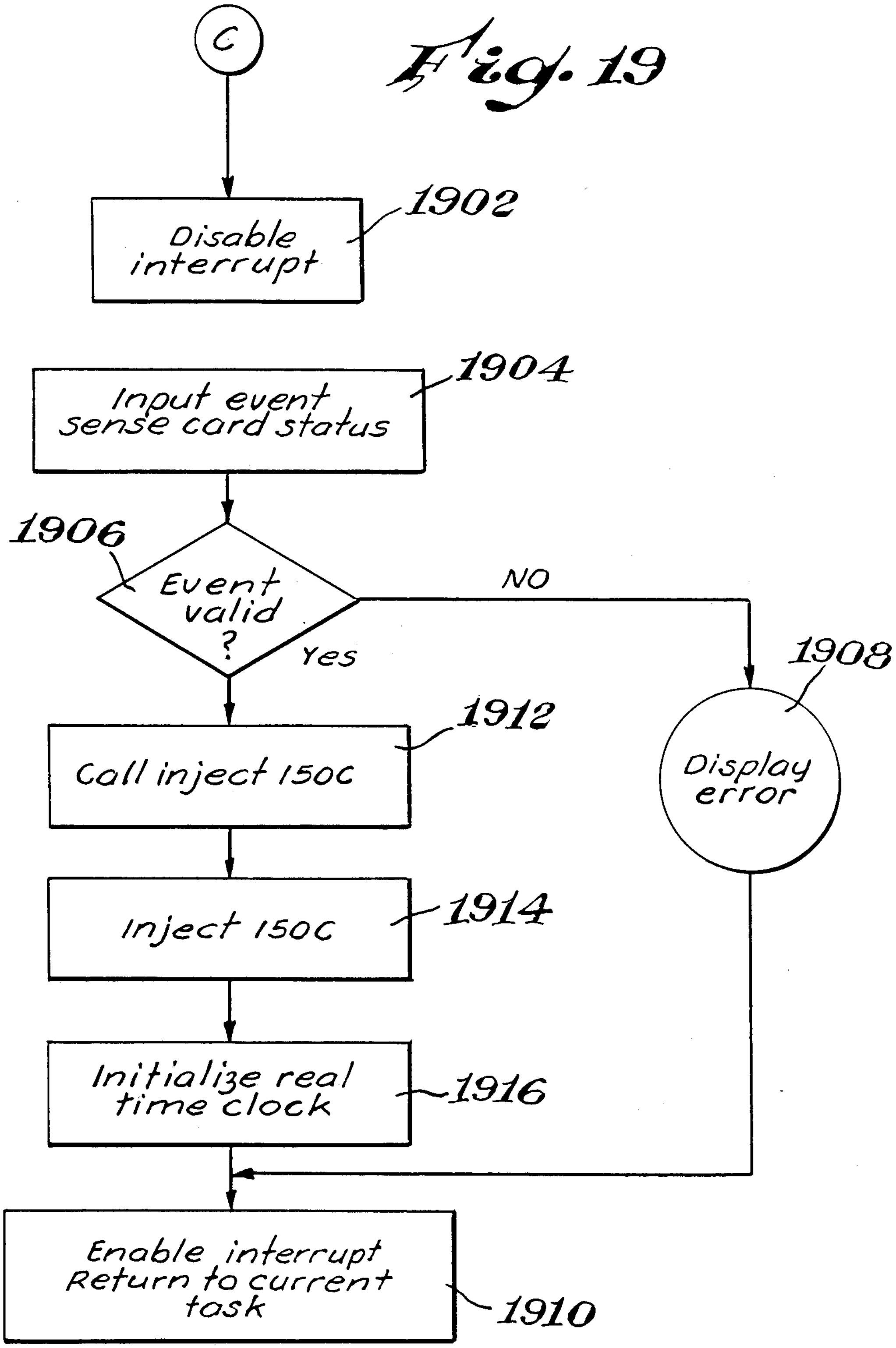
FIG. 19 is a representative example of a suitable computer program used to provide the event sense interrupt.

A representative example of the event sense service routine of block 1716 is shown in FIG. 19. First, a disable interrupt must occur, as indicated by block 1902. Thereafter, the particular event is prepared for a test, as indicated by block 1904. A decision block 1906 determines whether the sensed event is a valid one. If an invalid event is sensed, a display error is outputted to the user as indicated by block 1908. Thereafter, the program returns to its current task, as indicated by block 1910. In contrast, if the event that is sensed is determined to be valid, an Inject150C subprogram is called, as indicated by block 1912. The Inject150C subprogram performs certain functions, such as determining the run number, initialization of the arrays where the sampled data is stored, initialization of counters, and the setting of certain flags. The Inject150C subprogram is referenced by block 1914. Thereafter, initialization of appropriate real time clocks for subsequent analog to digital samplings is performed, as indicated by block 1916. These real time clock interrupts are provided by the programmed control of two HP98035A Hewlett-Packard Real Time Clocks ATREF runs are set up for 75 second intervals between interrupts. After the initialization has been performed in block 1916, the program returns to its current task, as indicated by block 1910. Any suitable program that can perform the desired event sensing can be used by the present invention.

The lowest priority interrupt, interrupt W, is used to read data that has been inputted on the keyboard of the present invention. First, when the keyboard interrupt goes high, as indicated by block 1718, the Systemkbd program is called, as indicated by block 1720. The Systemkbd program and supporting subroutines allow the present invention to read the data that has been inputted by the user on the keyboard. Representative flow charts illustrating the function of the programs can be found in FIGS. 21A and 21B. The overall operation of these programs allows detection of the particular input keys that have been activated by the user, and their subsequent conversion to usable data.

Figure 21A:
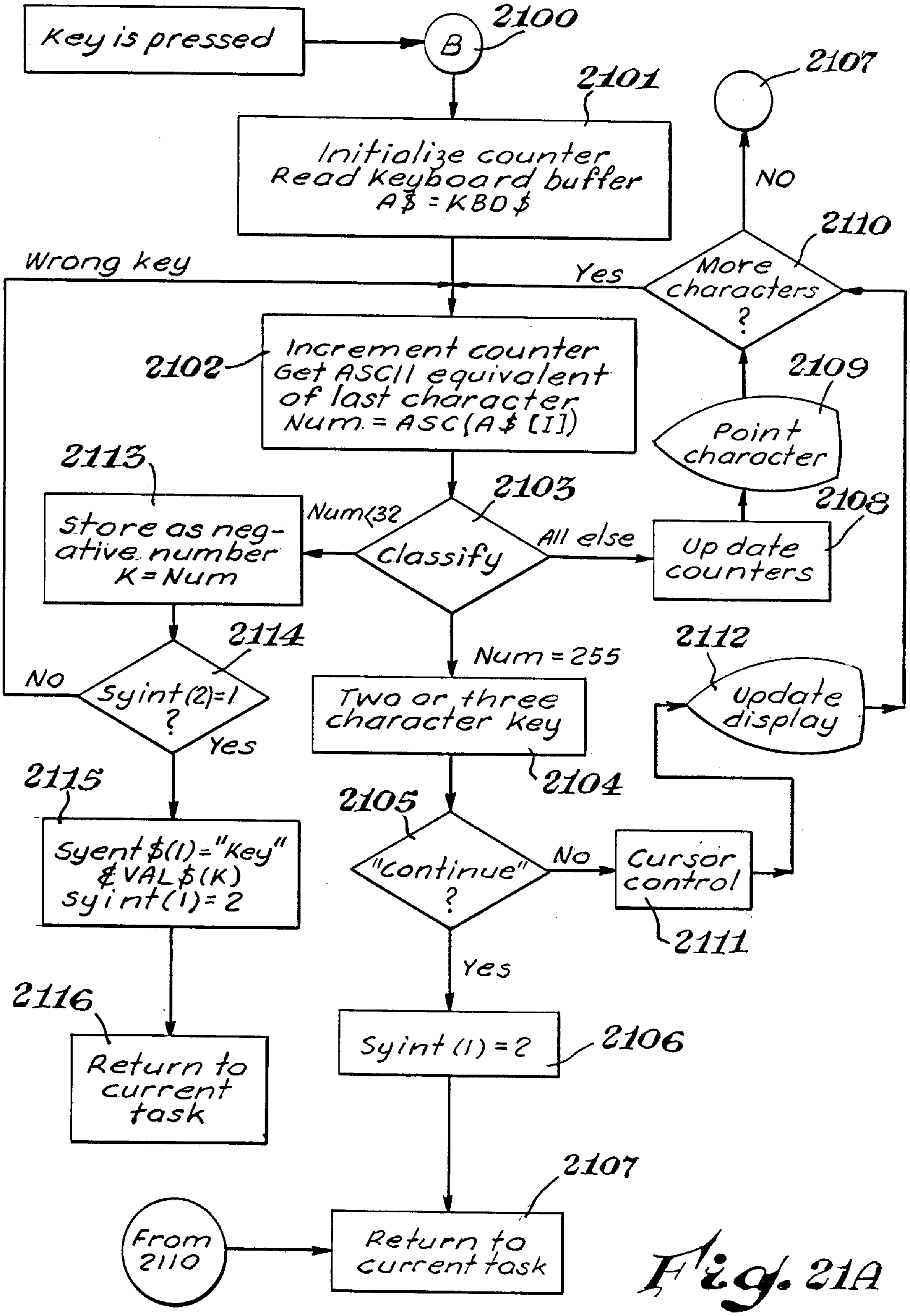
FIGS. 21A and 21B comprise a flow chart of a representative computer program used to provide the system keyboard interrupt (named "Skystemkbd").
Figure 21B:
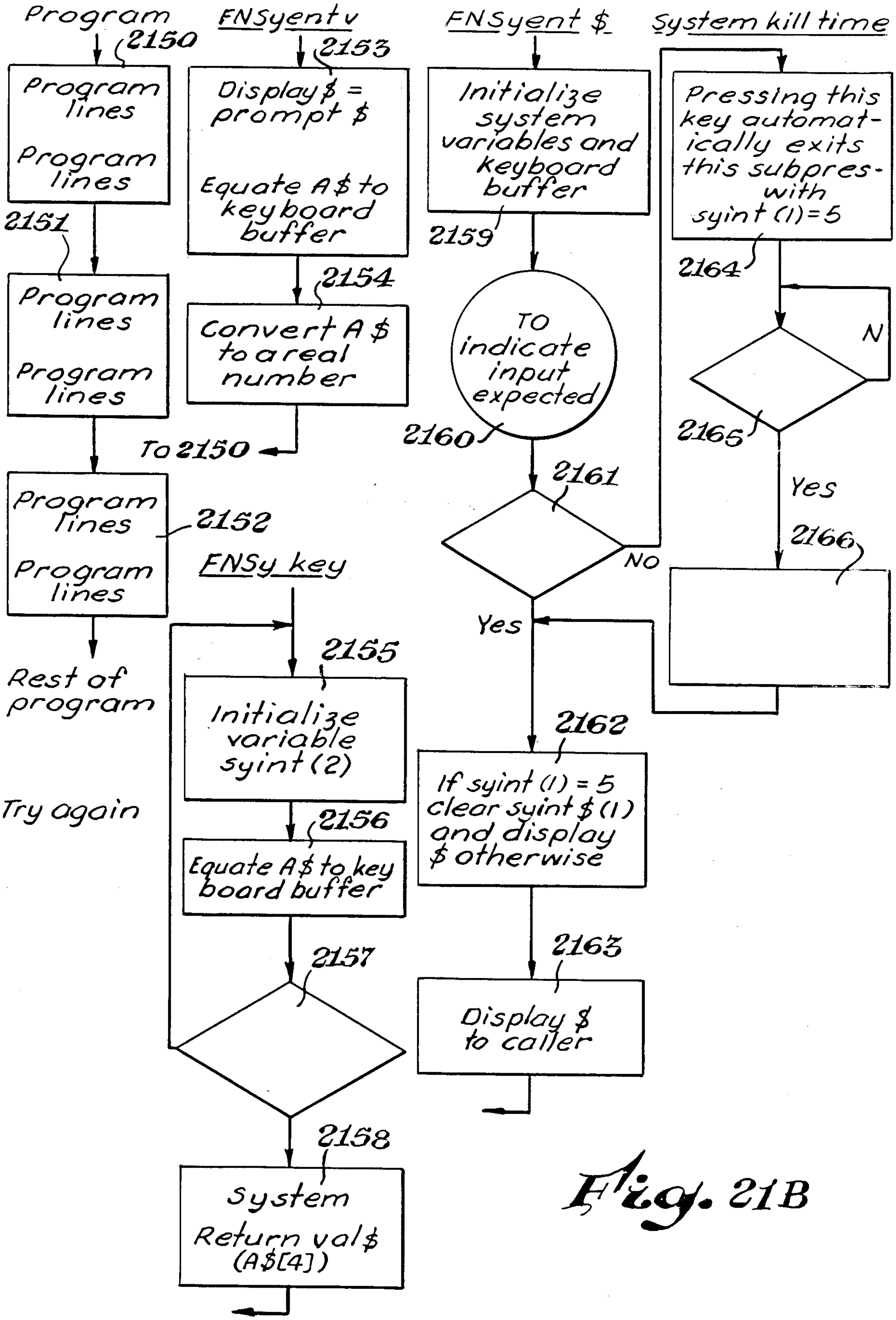

A thorough explanation of the detailed operation of these subroutines shown in FIGS. 21A and 21B is unnecessary, since any number of commercially available data collection software systems may be substituted, which allow for user interaction during the actual data acquisition. However, referring again to FIGS. 21A and 21B, a few of the pertinent points will be addressed.

As keys are pressed at the keyboard, the system interrupt will call Systemkbd and enter at circle 2100. This subroutine reads the keyboard buffer, as indicated by a block 2101, and converts each character sequentially to an integer in a block 2102. The magnitude of this integer then determines future activity in a decision block 2103. A single key in some cases generates more than one such integer; but these codes always begin with the integer 255. Also, all user input (except for system keys) is terminated by pressing the "CONTINUE" key on the HP9845 keyboard. This is a non-ASCII key and is the only action that decision block 2105 recognizes as the signal to inform the system that the operation is complete by setting system variable Syint(1) equal to 2 in block 2106.

A first example of three types of inputs is shown in block 2550 of FIG. 21B. The program needs the value of variable X. Thus, the string, Prompt$, might be set equal to "Enter the value of X" in a previous line. The system function call to FNSyentv passes the value of Prompt$ to block 2153, where processing begins. In block 2153, Prompt$ and Display$ are equated, then an additional system function call to FNSyent$ (block 2159) occurs. All the input routines have FNSyent$ in common, and this is where the keyboard is actually read. First, the system variables Syint(1) and Syent$(1) are initialized. Then, in block 2160, the value of display$, which in this case is "Enter the value of X" is printed at the terminal (not shown). The decision block 2161 calls Systemkilltime (block 2164). Systemkilltime is repeated until the value of Syint(1) allows a "yes" branch to indicate completion. As previously mentioned, this can only occur in block 2106 (or block 2115 for the system keys). Thus, the completion of input subroutines in FIG. 21B all depends upon the decision block 2105 in FIG. 21A to indicate that "CONTINUE" was pressed. Until this event occurs, all these routines spend the majority of their time in the "NO" cycle at block 2165 in Systemkilltime.

The other two input subroutines are FNSykey and FNSyent$ beginning at block 2155 and block 2159, respectively. FNSykey is used when the system expects the user to press a system key. The software is mostly menu driven, and menu selection corresponds to one of up to sixteen system keys. When Systemkbd detects a system key in decision block 2103, a special string is built in the keyboard buffer. The first three characters are "Key" and the string equivalent of the negative value of the key number is appended.

In the case of a system key press, the Systemkbd routine does not require the terminating "CONTINUE" key. After the special string is constructed and placed in the keyboard buffer, the system variable Syint(1) is set equal to 2 in block 2115. Thus, when FNSyent$ returns the contents of the keyboard buffer, the decision block 2157 checks to verify that it is a special string by looking for "Key". In the last example (block 2152), where an actual string is expected as input, the system function FNSyent$ is called directly.

These routines work together to allow the efficient processing of keys into real variables, string variables, or program requests (for system keys); this is all done without disrupting the flow of any data acquisition in progress.

What should be appreciated from the foregoing is that the present invention allows the acquisition of data to be taking place for a given polymer sample (foreground processing) while allowing the user to analyze data from another polymer sample (background processing). In this way, data acquisition can be taking place for one experiment, while the results of another experiment are being analyzed. This allows the hardware and software of the present invention to be utilized for more than one test setup.

Turning now to the analysis programs that are used to analyze the data stored in the arrays for a given polymer sample, a main menu displays the various programs that can be called by the user, as indicated by block 1722 in FIG. 17.

The main menu displays to the user eleven different programs that can be called. These are listed in Table I.

TABLE I

| |
|---|
| K0-COPY MASTER TYAPE TO T14 |
| K1-GPC Data Reduction |
| K2-To change Status |
| K3-STATUS program |
| K4-To change-out the DATA TAPE |
| K5-AUXILIARY Programs |
| K6-Atref Reductions |
| K9-Sample entry Program |
| K8-STDDIG REVIEW Program |
| Shift, Control, K14-Live Keyboard |
| Shift, Control, K14-Controlled shutdown |
| Select a Key |
| ATREF REDUCTION PROGRAM |
| Make sure the X-Y PLOTTER is on at this time. |
| K1-REGULAR REDUCTION |
| K2-Viscosity Data |
| K3-Overlays |
| K4-Include Purge |
| K7-Change Mass Storage Device from:T14 |
| K15-EXIT |
| Select a Key |

For example, the user can select program 0, which allows the user to copy a new system tape. Alternately, the user can select program 1, which allows for GPC data reduction. The user can select program 2, which allows the change of status of any instrument in terms of acquiring or not acquiring data. Program 3 indicates to the user the status of the present invention. Program 4 allows the user to change the output data tape. Auxiliary programs (not discussed) can be accessed with program 5. The SEC columns can be calibrated using program 8, and up to sixteen samples can be entered using program 9, so that the system takes data continuously. Program 9 informs the system what the run numbers will be and whether the analysis is to be SEC or ATREF. A controlled shutdown of the entire system can be performed using program 146. The keyboard can be made live using program 147 for modification and/or copying the current program.

In order to select one of these programs, the user must press a valid system key (or special function key) indicative of the program being selected, as indicated by block 1724. After the system senses the inputted character, it must determine whether it is a valid one, as indicated by decision block 1726. An invalid input causes the program to return back to the main display menu (block 1722). However, a valid input causes block 1726 to call the desired program.

The remaining program, program 6, which can be selected by the user, is of the main importance in connection with the present invention. This ATREF reduction program allows the raw mass detector data Wdata and the differential pressure data Dp, which typically are stored in suitable arrays, to be analyzed to produce the desired output, such as instantaneous specific viscosity spv data, instantaneous concentration c data, instantaneous intrinsic viscosity Intv data, and instantaneous viscosity average molecular weight data $Mv_i$ of the various fractions.

Figure 18D:
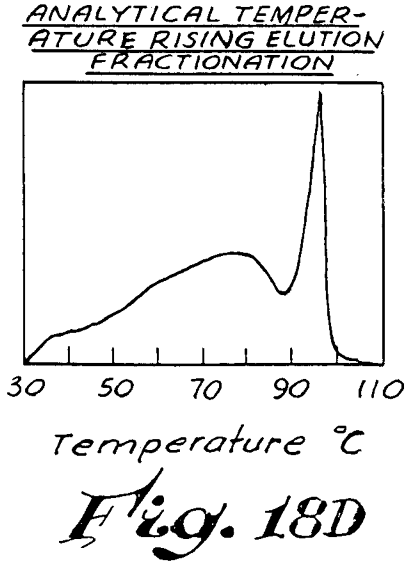
FIG. 18D is a typical plot of ATREF reduced data for a regular reduction.
Figure 18A:
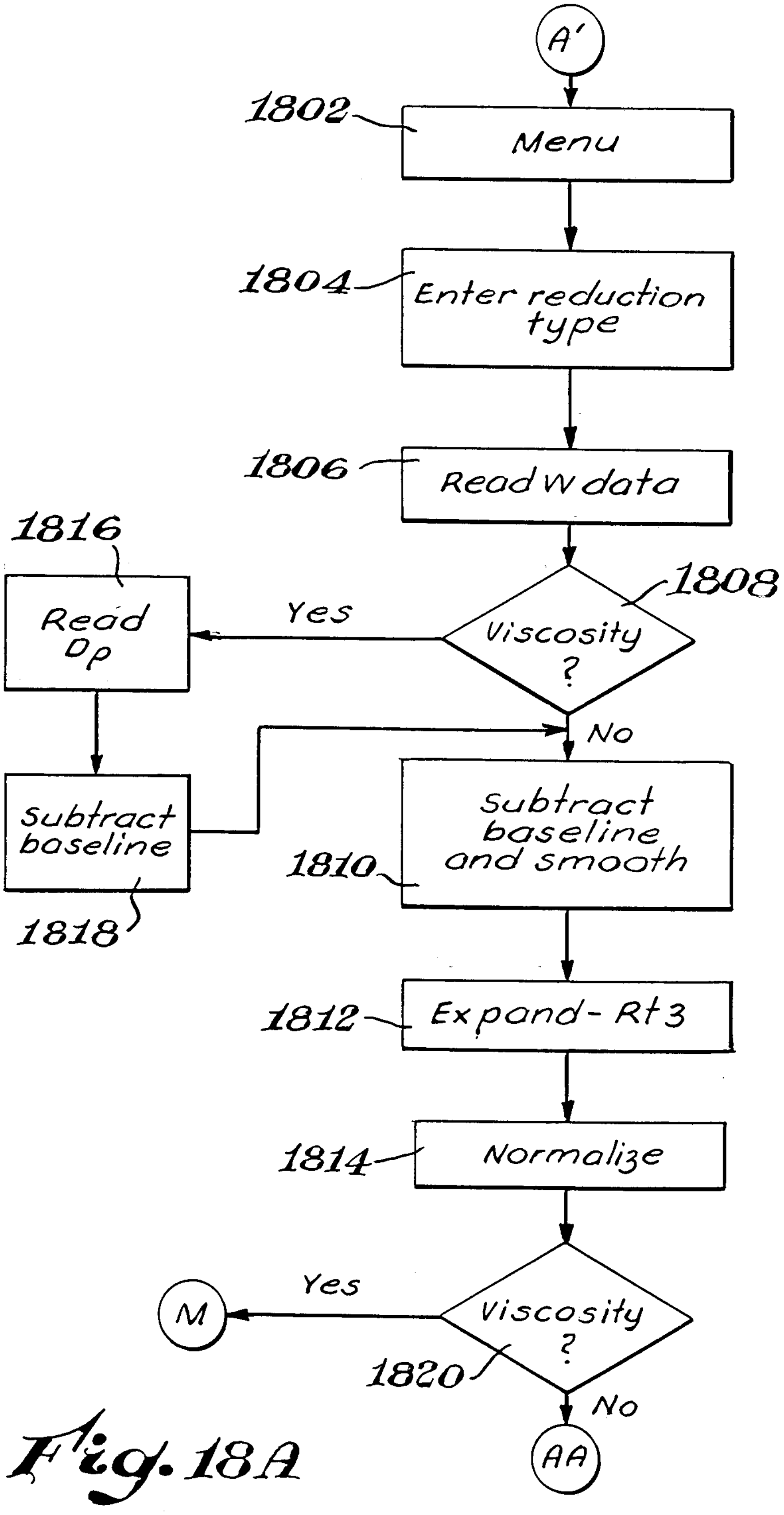
FIG. 18A is a flow chart of the first half of the data reduction algorithm.
Figure 18B:
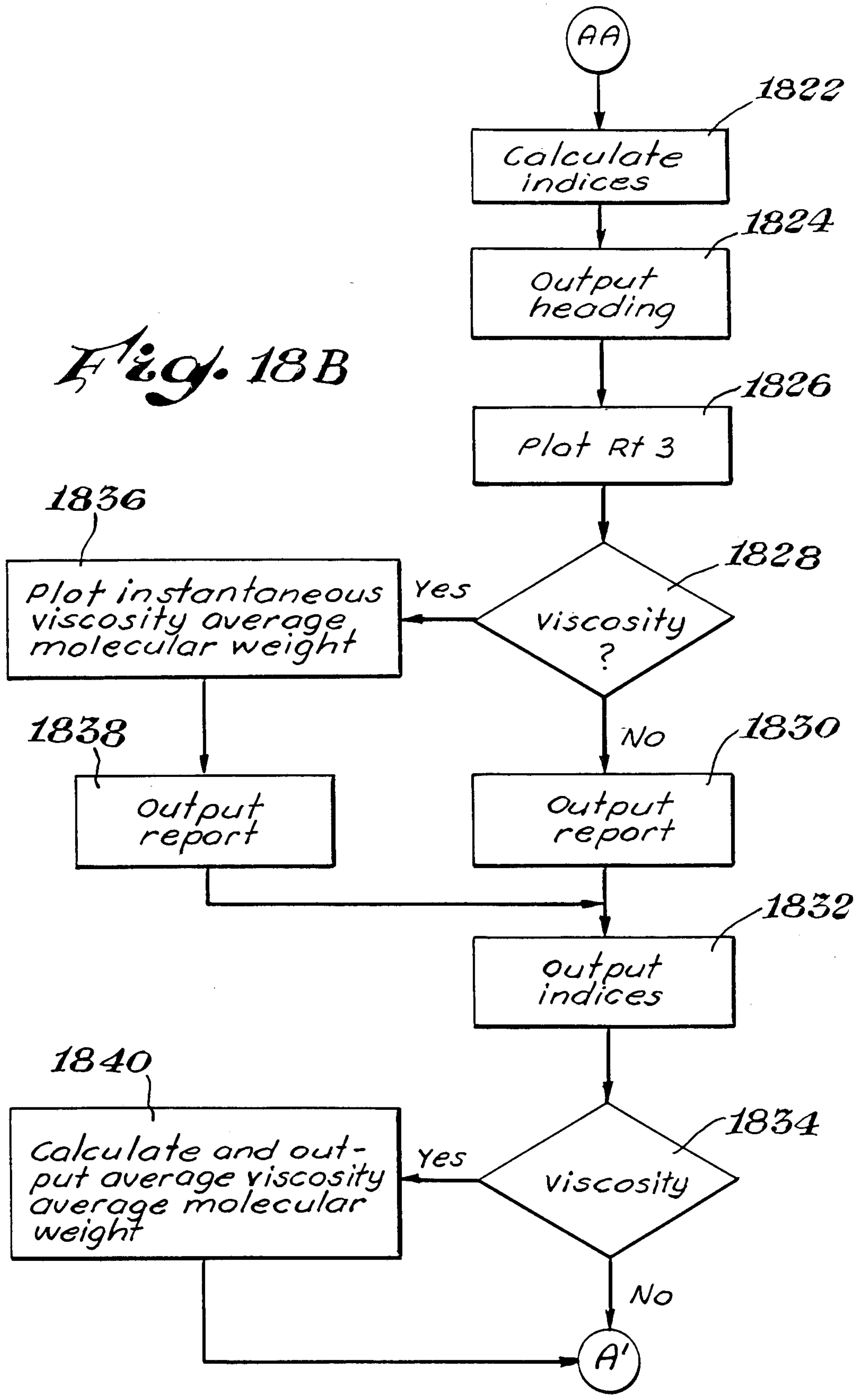
FIG. 18B is a flow chart of the second half of the data reduction algorithm.
Figure 18C:
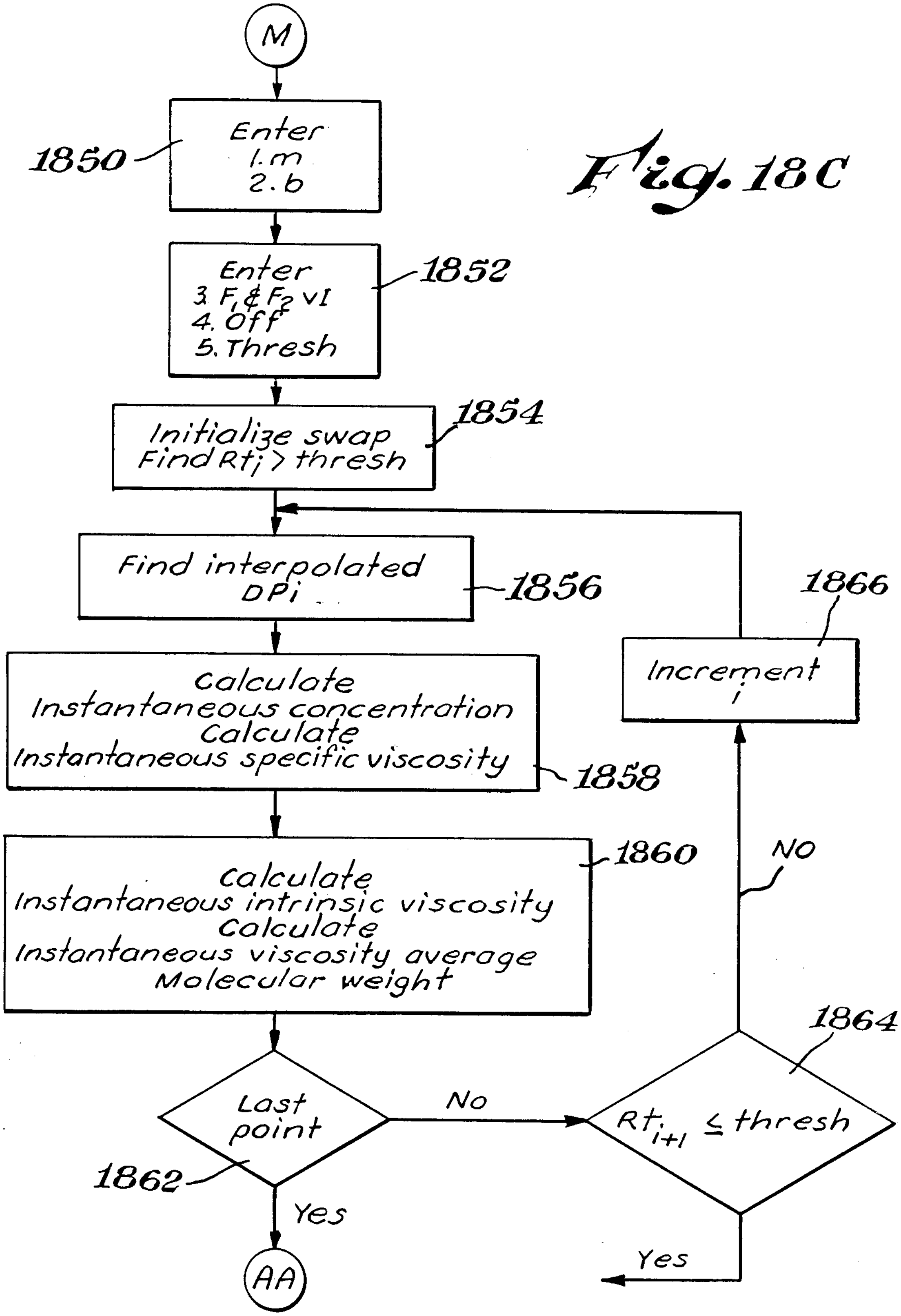
FIG. 18C is the section of the reduction software of the present invention that uses the mass detector data Wdata and the differential pressure data Dp to produce the instantaneous specific viscosity Spv data, instantaneous concentration c data, instantaneous intrinsic viscosity Intv data, and the instantaneous viscosity average molecular weight data $Mv_i$ of the various practices.

Referring now to FIGS. 18A, 18B and 18C, a flow chart of a representative program for implementing the ATREF data reduction is shown. This program implements the analysis strategy set forth above in section III of the Detailed Description.

Referring now to FIG. 18A, a display menu (Table II) is first provided to the user, as indicated by block 1802. The user typically can select from two types of reductions depending upon whether or not viscosity data is to be included. Other user inputs include the run number desired, the title and any comments to appear on the final report, and the name to whom the report is directed. These input subroutines are used in block 1804, and are discussed above in this section of the specification. A representation of this user/machine dialog is shown in Table II.

TABLE II

| ENTER THE ID NUMBER OF THE SAMPLE YOU WANT (NEG # GETS RECORD) |
|---|
| Explanation: User enters n<br>n = sample<br>Enter information for sample - n<br>1-ID NUMBER OF CUSTOMER<br>4-MELT INDEX (input a '0' if no MI is given)<br>5-DENSITY (Input a .'9' if no DENSITY is given.)<br>6,7,8-OTHER CUSTOMERS (Input'0' for EACH IF no other customers.)<br>Explanation: User enter 8 #'s separated by commas<br>FOR SAMPLE n<br>PUT A COMMA BETWEEN EACH ENTRY<br>1-SHORT STRING (25) (THIS WILL GO ON PLOT)<br>2,3-LONG STRINGS (30) (WILL ONLY APPEAR ON PRINTOUT)<br>Explanation: User enters 3 strings separated by commas |

Next, as shown in FIG. 18A, the data corresponding to the run number requested is read from the tape into a reserved variable array, as indicated by block 1806. The program of the present invention determines whether the viscosity data was requested (by the system key K2 actuated in the menu of Table I), as indicated by decision block 1808. If the answer is no (K2 is not selected), the program proceeds with a regular ATREF reduction, which produces only weight percent versus temperature data.

The computer program of the present invention includes the regular ATREF reduction (which is the regular, branch distribution only, type of data reduction) together with a data reduction algorithm which uses raw mass detector data Wdata and differential pressure data Dp to produce the instantaneous concentration c data and the instantaneous viscosity average molecular weight $Mv_i$ data for the various fractions. For simplicity, the operation of "regular" ATREF reduction will be discussed first. This part of the program of the present invention is still fundamental since it establishes the necessary link between mass distribution and elution temperature. Next, the aspects of algorithm of the present invention used to calculate instantaneous viscosity average molecular weight $Mv_i$ will be discussed.

Beginning with block 1810, the raw mass detector data (12 bit integers, for example), Wdata, from block 1806 is first converted to a real array Rt. By real array, we mean an array made up of real numbers as opposed to integers. Real array Rt is then smoothed using an algorithm, for example, similar to Park and Graessley, *J. Polym. Sci. Polym. Phys. ed.*, 15: 71 (1977). Note that any other type of suitable smoothing algorithm can be used.

The smoothed, real array Rt is baseline corrected to produce an adjusted array Rt. By baseline correction, we mean that the data values in the array are adjusted to reflect the background detector(s) responsible before signal(s) due to eluted polymer. This adjusted array Rt is used to create an expanded real array Rt3, as indicated in block 1812. The larger (10×) real array Rt3 is created by a suitable interpolation technique, such as Stirling's Central Difference Formula (J. B. Scarborough, *Numerical Mathematical Analysis* (1958), p. 74). This interpolation procedure adds nine interpolated values between each of the original values in Rt to produce the expanded array Rt3. Expanded real array Rt3 is used to approximate the total area of the mass detector response due to polymer.

Finally, as indicated by block 1814, the expanded array Rt3 is normalized by setting each element of the array equal to the quotient of itself and the sum of all the elements of the array. This provides a normalized expanded real array Rt3, which contains incremental weight percent data for each 0.1° C. of temperature rise (note that the original integer array Wdata was acquired at 1° C. intervals).

The chosen format of the final report for the regular ATREF of the present invention is similar to that represented programatically in the flow chart of FIG. 18B. The normalized expanded array Rt3 from block 1814 is provided by decision block 1820 when no viscosity data is included to block 1822 of FIG. 18B.

Selected distribution indices are then calculated in block 1822. These distribution indices, which are shown on the bottom of the printout of Table III are beyond the scope of the present invention and therefore are not described in detail. Next, heading, title (sample name, etc.) and comments are outputted to the line printer (not shown), as indicated by a block 1824. A plot, as indicated by block 1826, of the normalized expanded array Rt3 is produced on an incremental plotter (not shown) indicating weight percent (ordinate) versus temperature (abscissa), as shown in FIG. 18D. Next, decision block 1828 determines whether viscosity data was selected by the user. If the answer is no, the program proceeds to a block 1830.

A listing of the distribution is outputted to the printer (not shown), as indicated by block 1830. Referring now to Table III which is representative, the listing is as follows. For each 2° C. increment in temperature beginning at 24° C. to 26° C., the temperature of the upper bound is printed under the "Temperature" heading, the mass detector response at the upper temperature boundary with the background subtracted (represented by Rt) is printed under the "Ht Obs", which is an abbreviation for "Height Observed".

TABLE III

| Temperature | Ht Obs | Frac Pct | Cum Pct |
|---|---|---|---|
| 32.0 | 9.0 | .2 | .2 |
| 34.0 | 40.8 | .7 | .8 |
| 36.0 | 58.1 | 1.0 | 1.8 |
| 38.0 | 59.7 | 1.0 | 2.8 |
| 40.0 | 68.0 | 1.1 | 4.0 |
| 42.0 | 74.3 | 1.3 | 5.2 |
| 44.0 | 78.8 | 1.3 | 6.6 |
| 46.0 | 86.5 | 1.5 | 8.0 |
| 48.0 | 92.8 | 1.6 | 9.6 |
| 50.0 | 104.4 | 1.8 | 11.4 |
| 52.0 | 112.6 | 1.9 | 13.3 |
| 54.0 | 120.9 | 2.1 | 15.4 |
| 56.0 | 139.1 | 2.3 | 17.7 |
| 58.0 | 152.0 | 2.6 | 20.3 |
| 60.0 | 166.0 | 2.8 | 23.1 |
| 62.0 | 174.7 | 3.0 | 26.1 |
| 64.0 | 191.2 | 3.2 | 29.3 |
| 66.0 | 207.0 | 3.5 | 32.8 |
| 68.0 | 214.8 | 3.6 | 36.4 |
| 70.0 | 217.9 | 3.7 | 40.1 |
| 72.0 | 221.5 | 3.8 | 43.9 |
| 74.0 | 228.8 | 3.9 | 47.8 |
| 76.0 | 231.1 | 3.9 | 51.7 |
| 78.0 | 228.5 | 3.9 | 55.6 |
| 80.0 | 226.2 | 3.8 | 59.4 |
| 82.0 | 215.5 | 3.7 | 63.1 |
| 84.0 | 200.8 | 3.4 | 66.5 |
| 86.0 | 178.7 | 3.0 | 69.5 |
| 88.0 | 153.3 | 2.6 | 72.2 |
| 90.0 | 150.1 | 2.6 | 74.7 |
| 92.0 | 196.9 | 3.4 | 78.1 |
| 94.0 | 351.2 | 5.9 | 84.0 |
| 96.0 | 563.2 | 9.1 | 93.1 |
| 98.0 | 293.1 | 5.4 | 98.5 |
| 100.0 | 49.1 | 1.0 | 99.5 |
| 102.0 | 14.1 | .2 | 99.9 |
| 104.0 | 8.2 | .1 | 99.8 |
| 106.0 | 7.0 | .1 | 100.0 |

SCB AVERAGE TEMPERATURE = 65.2
STANDARD DEVIATION = 13.5
AVERAGE TEMPERATURE = 73.7
STANDARD DEVIATION = 17.4

The sum of the elements in the normalized expanded real array Rt3 between the lower (inclusive) and upper (exclusive) temperature boundaries are printed under the heading "Frac Pct", which is an abbreviation for "fractional percent". Finally, the running sum of the elements in the normalized expanded real array Rt3 up to the upper temperature boundary in the row that is being printed is printed under the heading "Cum Pct", which is an abbreviation for "cumulative percent". Referring again to FIG. 18B, this whole printing process is represented by block 1830. The selected distribution indices are then printed, as indicated by a block 1832. If decision block 1834 then indicates that viscosity data was not requested by the user, the program of the present invention proceeds back to block 1802 of FIG. 18A.

When viscosity data was requested by the user, decision block 1808 of FIG. 18A causes a block of viscosity data to be read into an integer array Dp, as indicated by a block 1816. This integer array Dp is representative of differential pressure data obtained concurrently with mass distribution data represented by the array Wdata described above. For simplicity, the terms viscosity data, viscosity points, and differential pressure data are used synonymously since the relationship between these terms are clearly defined in the equations 2 through 6. Thereafter, integer array Dp is baseline subtracted as described above to produce a baseline subtracted integer array Dp, as indicated by block 1818. The program proceeds to block 1810, and the computations are performed as described above.

When viscosity data is requested by the user, control is passed to branch M (FIG. 18C) the branch M to the subroutine is included. This subroutine calculates instantaneous specific viscosity Spv, instantaneous intrinsic viscosity Intv and the instantaneous viscosity average molecular weight $Mv_i$ for each of the 1° C. elements described above.

The use of viscosity data to obtain instantaneous viscosity average molecular weight was described theoretically in Sections I and III above. The preferred version of the program which implements this theory is shown in FIG. 18C. First, in blocks 1850 and 1852 of FIG. 18C, the user enters a few parameters necessary for subsequent calculations. These user supplied parameters are requested in the form of the following real variables:

1. m—least square slope of regression analysis on concentration and mass detector response (see equations 9 and 10a above);
2. b—least square intercept of the regression analysis on concentration and mass detector response;
3. $F_1$ and $F_2vI$ ($F_2vI$ is entered as the actual inlet pressure in Pascals observed during the run, for example, 19,000)—overall attenuation factors used to convert a 12 bit binary word to the corresponding viscosity needed for equation 7d above.
4. OFF—detector delay offset or the time lag between the contents of the mass detector and the viscometer; and
5. Thresh—a noise suppression value used in the calculation.

These values are entered in the appropriate units for the subsequent calculations.

Each of viscosity points in baseline subtracted integer array Dp is used in turn to calculate the corresponding instantaneous viscosity average molecular weight for that element. An example using an arbitrary element Dp: proceeds as follows: A new real array Swap is created to hold temporary results and the final instantaneous viscosity average molecular weight corresponding to each element i of the baseline subtracted integer array $Dp_i$. Each element in smoothed, baseline subtracted real array Rt is tested sequentially until the first value Rt greater than Thresh is found, as represented by a block 1854. The element in baseline subtracted integer array Dp corresponding to the above element Rt in smoothed, baseline subtracted real array Rt is element $Dp_i$.

Referring to a block 1856, we digress to define variable OFF. Even though the data in baseline subtracted integer array Wdata (mass detector response) and baseline subtracted integer Dp (pressure drop or viscosity data) are taken simultaneously, the corresponding elements in Wdata and Dp correspond to materials eluded at slightly different temperatures. This is due to the fact that the effluent containing polymer proceeds sequentially from the first detector to the second detector. This embodiment of the present invention routes the effluent first to the mass detector and then to the viscometer. The delay between when a polymer molecule resides in the mass detector and when the same molecule resides in the viscometer is referred to as the Offset. This delay offset is named OFF.

The delay offset OFF entered by the user in block 1852 is the time (in minute here) between the two detectors. It is used to calculate the corresponding viscosity points from baseline subtracted array Dp, which correspond to the same elution temperature as a particular baseline subtracted, smoothed real element Rt of the array Rt. Since there is little chance that OFF is exactly divisible by SI, the sampling interval between two consecutive detector responses (75 sec in the preferred embodiment), makes necessary interpretation between adjacent viscosity points in the baseline subtracted array Dp. The elements in baseline subtracted array Dp which are chosen for the interpolation are the two consecutive $Dp_{j-1}$ and $Dp_j$ which occur respectively just prior to and just after the time represented by SI*i+-OFF as measured from the beginning of the analysis. Therefore, the interpolated value to be obtained from baseline subtracted array Dp corresponding to the particular baseline subtracted real mass detector response Rt is Dp and is obtained by the following equation:

$$D_{pi} = D_{pj-1} + \left[\left(\frac{OFF}{SI} - (j-1-i)\right)*(DP_j - DP_{j-1})\right] \quad (14)$$

This equation (14) is a general formula and is applicable even where the value of SI is much smaller than the value of OFF. A block 1856 is a representation of the correction for the detector delay offset.

Referring now to block 1858, the value Rt referred in block 1856 is now used to calculate the instantaneous concentration c of the eluding polymer responsible for the pressure drop $Dp_i$. The instantaneous concentration c is calculated using equation 10(a) above and the values for user parameters m and b. (The r in equation 10a being replaced by each successive value of baseline subtracted, smoothed real array Rt.) Thereafter, the instantaneous specific viscosity Spv corresponding to pressure drop $DP_i$ is calculated using the user parameters $F_1$ and $F_2vI$ in equation 7(d) above.

Referring now to a block 1860, a new real array element $Mv_i$ is used to temporarily store the corresponding instantaneous intrinsic viscosity Intv obtained by dividing the instantaneous specific viscosity Spv by the instantaneous concentration c. This temporary result $Mv_i$ is then converted to the instantaneous viscosity average molecular weight by using equation 11. The constants K and 1/a are coded directly to obtain the following equation.

$$Mv_i = (40{,}900)\,(\text{Intv})^{1.44} \quad (15)$$

The value of the new real array element $Mv_i$ is therefore the instantaneous viscosity average molecular weight of that fraction of the polymer eluting between the temperature 24°+i°C. and 24°+(+1)°C.

Two possible outcomes determine the direction of the computer control as represented by decision blocks 1862 and 1864. The affirmative test in either case will terminate this subroutine by passing control back to block 1822 in FIG. 18B via connector M'. The first terminator asks whether cue of the data is exhausted, or more precisely: is $Swap_i$ the last element of the new real array Swap. The second termination asks whether the mass detector response of the next data point as indicated by $Rt_{+1}$ is less than Thresh. This last condition will occur at the end of the run.

Referring again to FIG. 18B, the heading, title and comments are outputting to the printer (not shown), as indicated by block 1824. The mass distribution data is outputted to the incremental plotter (not shown) as described above by block 1826. Decision block 1828 now indicates that viscosity data was selected by the user. The logarithm of the actual magnitude of the instantaneous viscosity average molecular weights stored in the new real array Swap are plotted (using "+" symbols in the representative plot of FIG. 24), as indicated by block 1836. Next, in a block 1838, a listing of temperature, detector responses, weight percents, cumulative weight percents, and instantaneous viscosity average molecular weights is produced by the printer (not shown).

This listing (a representative example of which is shown in Table IV) includes the following headings: "Temp", which is the elution temperature: "Ht Obs", which is the abbreviation for the baseline subtracted response for the viscometer Dp; "Frac Pct", height observed Rt for the mass detector: "Dp", which is an abbreviation for differential pressure for the baseline substracted response for the viscometer DP; "Fract Pct", which is an abbreviation for fractional percent of polymer eluting in the two degree centigrade interval; "Cum Pct", which is an abbreviation for cumulative percentage of the running total of the weight percent to the corresponding elution temperature; and "MOLECULAR Wt", which is an abbreviation for the instantaneous viscosity average molecular weight. The selected distribution indices are printed as before for regular ATREF in the block 1832.

TABLE IV

| Temp | Ht Obs | Dp | Frac Pct | Cum Pct | MOLECULAR Wt |
|---|---|---|---|---|---|
| 30.0 | 4.2 | 3 | .3 | .3 | 13331 |
| 32.0 | 11.5 | 9 | .7 | 1.0 | 16198 |
| 34.0 | 15.6 | 11 | 1.0 | 2.0 | 14630 |
| 36.0 | 16.0 | 11 | 1.1 | 3.1 | 13097 |
| 38.0 | 17.4 | 15 | 1.1 | 4.2 | 19509 |
| 40.0 | 20.0 | 18 | 1.3 | 5.5 | 20181 |
| 42.0 | 22.4 | 22 | 1.5 | 7.0 | 24636 |
| 44.0 | 25.4 | 27 | 1.7 | 8.7 | 26556 |
| 46.0 | 28.8 | 31 | 1.9 | 10.6 | 27484 |
| 48.0 | 32.8 | 37 | 2.2 | 12.7 | 29867 |
| 50.0 | 35.7 | 42 | 2.3 | 15.0 | 31733 |
| 52.0 | 37.9 | 47 | 2.5 | 17.5 | 35397 |
| 54.0 | 41.9 | 55 | 2.8 | 20.3 | 37562 |
| 56.0 | 45.9 | 60 | 3.0 | 23.3 | 38464 |
| 58.0 | 47.4 | 65 | 3.1 | 26.4 | 40951 |
| 60.0 | 48.3 | 71 | 3.2 | 29.6 | 44751 |
| 62.0 | 50.2 | 74 | 3.3 | 32.9 | 45014 |
| 64.0 | 51.4 | 75 | 3.4 | 36.3 | 45035 |
| 66.0 | 51.5 | 79 | 3.4 | 39.7 | 48486 |
| 68.0 | 51.0 | 82 | 3.4 | 46.4 | 51538 |
| 70.0 | 51.2 | 83 | 3.4 | 46.4 | 52255 |
| 72.0 | 52.1 | 87 | 3.4 | 49.8 | 54738 |
| 74.0 | 53.9 | 90 | 3.5 | 53.4 | 54596 |
| 76.0 | 53.3 | 89 | 3.5 | 56.9 | 54689 |
| 78.0 | 51.7 | 90 | 3.4 | 60.3 | 58080 |
| 80.0 | 47.7 | 88 | 3.2 | 63.4 | 63113 |
| 82.0 | 44.3 | 82 | 2.9 | 66.4 | 62698 |
| 84.0 | 41.4 | 77 | 2.7 | 69.1 | 63501 |
| 86.0 | 44.0 | 88 | 2.9 | 72.0 | 70417 |
| 88.0 | 58.8 | 133 | 3.9 | 75.9 | 85028 |
| 90.0 | 79.8 | 191 | 5.2 | 81.1 | 93185 |
| 92.0 | 91.7 | 238 | 6.0 | 87.1 | 105470 |
| 94.0 | 81.9 | 200 | 5.4 | 92.5 | 96232 |
| 96.0 | 62.9 | 162 | 4.2 | 96.6 | 102355 |
| 98.0 | 36.0 | 96 | 2.4 | 99.0 | 105874 |
| 100.0 | 12.1 | 35 | .9 | 99.9 | 106218 |

TABLE IV-continued

| Temp | Ht Obs | Dp | Frac Pct | Cum Pct | MOLECULAR Wt |
|---|---|---|---|---|---|

SCB AVERAGE TEMPERATURE = 24.0
STANDARD DEVIATION = 0.0
AVERAGE TEMPERATURE = 70.9
STANDARD DEVIATION = 17.7
Whole Polymer Intrinsic Viscosity = 1.27 E + 00
Mv = 5.73 E + 04
Weight Average Mv = 5.93 E + 04

Decision block 1834 then determines whether viscosity data was requested; if so, a block 1840 prints the overall average viscosity average molecular weight, abbreviated "Weight Average Mv". This value is arrived at in the usual manner. The weight percent of each 1° C. slice is multiplied by the instantaneous viscosity average molecular weight stored in the new real array Swap. And the final result, the sum of all the above multiplications, is the weight average. This value will not be the same as the true weight average molecular weight, but in general this value will be less than the true weight average. In most cases, it will therefore serve as a good indicator of the classical weight average molecular weight.

Having now generally described the invention, the same will become more readily understood by reference to the following examples which are not intended to be limiting unless otherwise stated. The first five examples are included to summarize the development and utility of ATREF, while the final examples demonstrate the use of HTCV ATREF.

V. EXAMPLES

EXAMPLE 1

Figure 6:
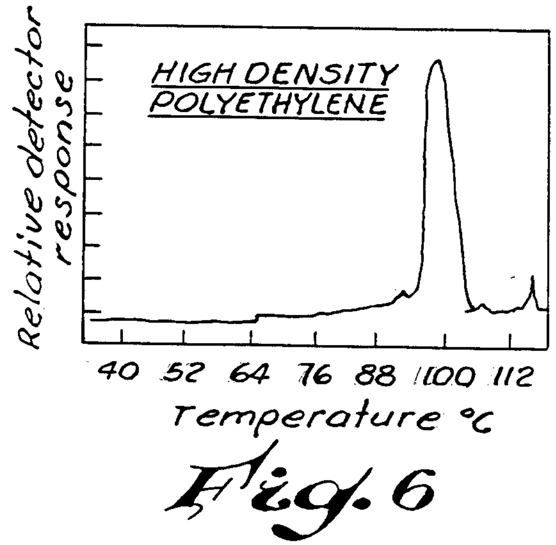
FIG. 6 is a graph of ATREF data for a 10 MI, 0.962 g/cc density solution of polyethylene. The ordinate is the relative concentration of eluted polymer; the abscissa is the elution temperature.

FIG. 6 shows the ATREF data for a 10 MI (melt index), 0.962 g/cc density solution process polyethylene (HDPE). This resin was selected in order to see if the ATREF system would show the expected absence of low crystallinity fractions and the presence of a large amount of high crystallinity fraction. The vertical axis is the response to concentration of polymer in solution at 135° C. as it is eluted from the column and passed through the DRI. The horizontal axis is the linear increase in temperature of the heating oil in which the column was heated. The temperature programmer (Haake PG-20) is seen to have produced a very good linear response of temperature versus time. Chart speed was constant at 5 cm/hr. The "hash" marks along the concentration curve are 5 ml syphon dumps of eluant polymer solution generated in the conventional manner with a carefully measured syphon tube and a relay activated by a photocell. A constant horizontal spacing of the marks indicates a constant flow rate of solution through the refractometer sample cell. For the early developmental samples, eluant was automatically collected every 20 minutes (4° C.) in order to measure molecular weight distributions of the ATREF fractions by SEC. The event marks at the top of FIG. 6 represent the fraction collection (#1–#21).

Since the increase in column elution temperature results in the solubility of polymer fractions of increasing crystallinity (or decreasing frequency of short chain branching), the horizontal axis in FIG. 6 can be regarded as the axis of increasing crystallinity. The absolute percent crystallinity of the fractions is inferred from preparative scale TREF fractions, and the crystallinity can in principle be deduced from the associated column elution temperatures.

From the ATREF curve profile of the solution, it was concluded that:

(1) the polymer had practically no detectable fraction of low crystallinity:

(2) most of the polymer eluted in the high crystallinity range of 95° to 105° C. (it should be noted that all polyethylene thus far studied in the TCB solvent system were completely eluted by 105° C.):

(3) the crystallinity distribution was narrow, indicating a material very uniform or homogeneous in crystallinity.

Figure 7:
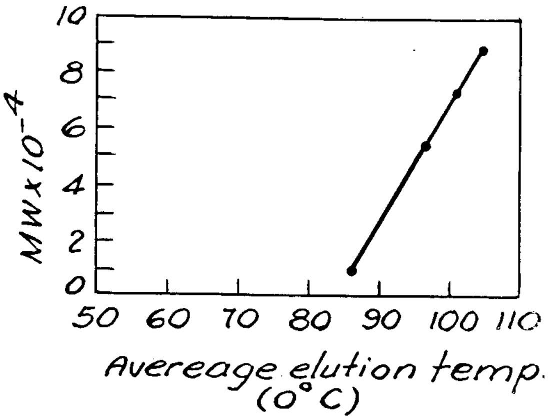
FIG. 7 is a graph of the data presented in Example 1. The ordinate represents molecular weight $(Mw)\times 10^{-4}$ as measured by SEC: the abscissa represents elution temperature in degrees centigrade.

The low levels of polymer fraction seen eluting in the 80° to 90° C. region of the curve indicate the presence of slight amounts of lower crystallinity material. This is likely to be the lower molecular weight portions of the polymer in which the higher relative amount of chain ends act to reduce crystallinity. Table V below supports this observation. FIG. 7 indicates that the weight average molecular weight (Mw) of the fractions does indeed decrease as fraction elution temperature (that is, crystallinity) decreases Note that $M_p$ (peak molecular weight) is defined as the most probable molecular weight, and $M_n$ is the number average molecular weight. These molecular weights were derived from subsequent analysis by SEC of the fractions referred to above.

TABLE V

MW DATA ON ATREF FRACTIONS OF EXAMPLE 1

| FRACTION (ATREF 16) | COLUMN ELUTION TEMPERATURE, °C. | $\overline{Mn} \times 10^{-4}$ | $\overline{M} \times 10^{4}$ | MP $\times 10^{-4}$ | $\overline{Mw}/\overline{Mn}$ |
|---|---|---|---|---|---|
| 16 | 84–88 | 0.722 | 0.909 | 0.832 | 1.26 |
| 19 | 95–99 | 1.93 | 5.33 | 1.66 | 2.76 |
| 20 | 99–103 | 2.40 | 7.09 | 3.36 | 2.95 |
| 21 | 103–107 | 3.14 | 8.79 | 3.84 | 2.80 |

EXAMPLE 2

Figure 8:
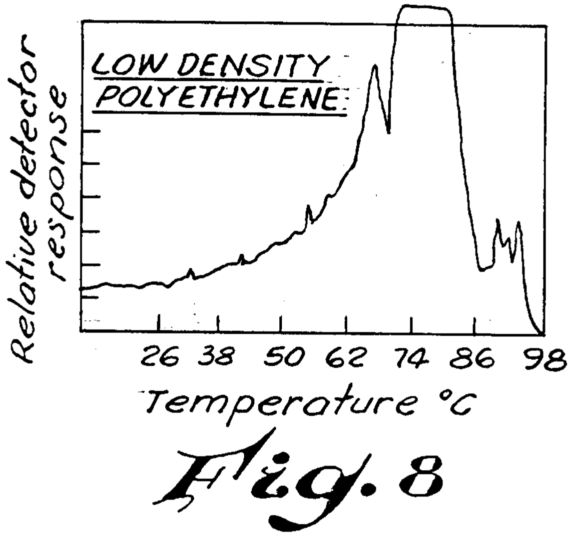
FIG. 8 is a graph of ATREF data for the LDPE of Example 2. The ordinate represents relative concentration of eluting polymer while the abscissa represents elution temperature.

FIG. 8 shows the ATREF curve for LDPE, produced under the same operation conditions as previously described in Example 1. The bulk of the polymer eluted in the crystallinity range corresponding to an elution temperature interval of approximately 70° to 85° C. The crystallinity distribution for this sample was relatively narrow. There were also detected smaller amounts of polymer eluting in the lower crystallinity region. This could have been material of higher level of short chain branching or lower molecular weight or both. The peak of the HDPE was centered at 100° C. Such a difference is a reflection of the much lower total crystallinity (and density) of the LDPE relative to the HDPE.

Figure 9:
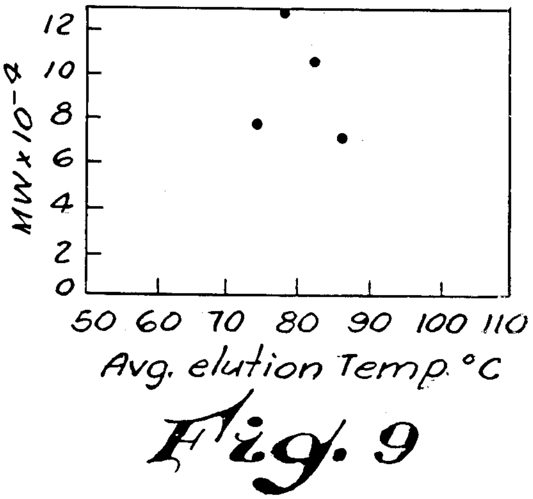
FIG. 9 is a graph of the data from Table II comparing molecular weight (ordinate) against elution temperature (abscissa).

The data of Table VI below and FIG. 9 present molecular weight data on four of the LDPE fractions collected across the large peak of the ATREF curve of FIG. 8. The fraction molecular weights did not show any consistent pattern with elution temperature.

TABLE VI

| MW DATA ON ATREF FRACTIONS OF EXAMPLE 1 | | | | | |
|---|---|---|---|---|---|
| FRACTION (ATREF 13) | COLUMN ELUTION TEMPERATURE, °C. | $\overline{M}n \times 10^{-4}$ | $\overline{M} \times 10^4$ | MP $\times 10^{-4}$ | $\overline{M}w/\overline{M}n$ |
| 14 | 72–76 | 2.42 | 7.66 | 3.59 | 3.17 |
| 15 | 76–80 | 3.45 | 12.9 | 4.83 | 3.74 |
| 16 | 80–84 | 3.44 | 10.6 | 4.24 | 3.09 |
| 17 | 84–88 | 3.16 | 7.07 | 3.97 | 2.24 |

EXAMPLE 3

Figure 10:
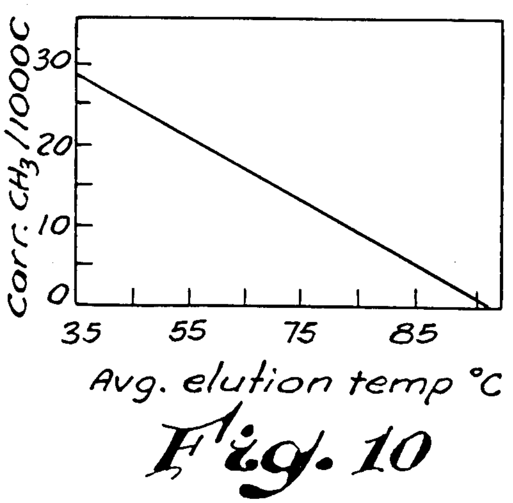
FIG. 10 is a graph of branching ($CH_3$/1000) against elution temperature for preparative scale fractions of an ethylene-octene copolymer A.

The remainder of the temperature rising elution fractionation studies, both preparative and analytical, have been done using only ethylene/octene copolymer produced in the Ziegler catalyzed solution process. Calibration of ATREF, so that column elution temperature may be related to the corresponding value of short chain branching (as $CH_3/1000$ carbon atoms), has been accomplished using preparative fractions of such a resin, which possesses very broad branching distribution characteristics. See FIG. 10.

Figure 11:
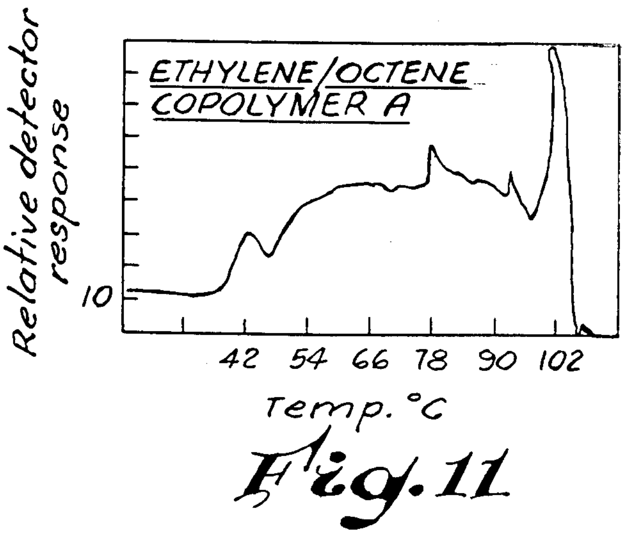
FIG. 11 is a graph of the ATREF crystallinity distribution for copolymer A. Relative concentration is plotted on the ordinate and elution temperature on the abscissa.

FIG. 11 is the ATREF crystallinity distribution curve for the above resin. Comparing FIG. 10 to that of FIG. 11, showing similar data gathered from the preparative fractionation of the same sample, points out the most important advantage of the analytical technique over the preparative: that is, the ability to define a continuous weight distribution curve in the former case compared to only a 14 data point curve in the latter.

Since a calibration relationship has been established between column elution temperature and approximate octene content of the corresponding fraction for this resin type (see FIG. 10), the crystallinity axis of FIG. 11 may be expressed in terms $CH_3/1000$ C. The approximately 30° C. elution temperature corresponds to about 30 octenes/1000 C, while the approximately 100° C. elution temperature represents polymer fraction having practically zero short chain branching: i.e. HDPE.

It is apparent that the ATREF curve for these octene copolymerized polyethylenes is quite different from that for HDPE (FIG. 6) or LDPE (FIG. 8). There is a considerable amount of the whole polymer having a high octene (low crystallinity) content (the average $CH_3/1000$ value in the sample resin in about 12) as well as a significant amount of polymer that is of essentially zero octene content (high crystallinity, HDPE). The ATREF curve profile indicates that the resin possesses a broad distribution of crystallinities. Such a distribution reveals that this has an "uneven" or non-homogeneous dispersion of the octene comonomer throughout the whole polymer (at least from the intermolecular standpoint).

EXAMPLE 4

Figure 13:
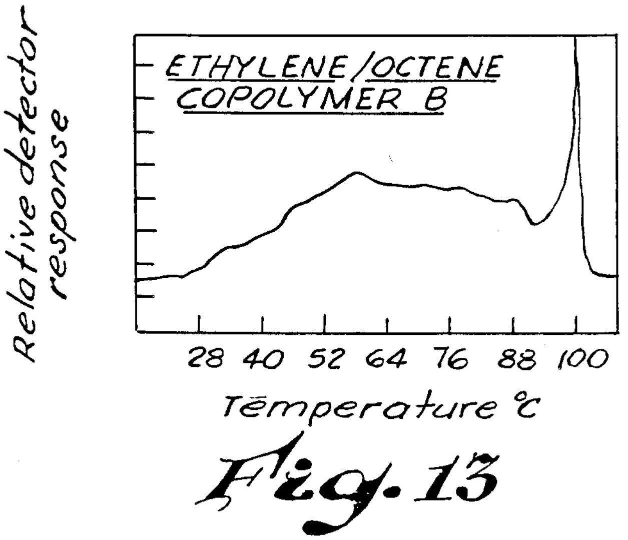
FIG. 13 is a graph showing the ATREF crystallinity distribution for Example 4, ethylene-octene copolymer B. Relative concentration is plotted on the ordinate and elution temperature is plotted on the abscissa.
Figure 14:
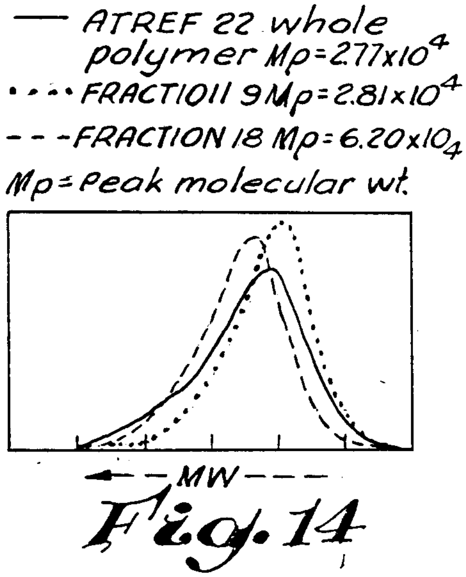
FIG. 14 is a plot of the data of Table III, plotting molecular weight (abscissa) against elution temperature.
Figure 15:
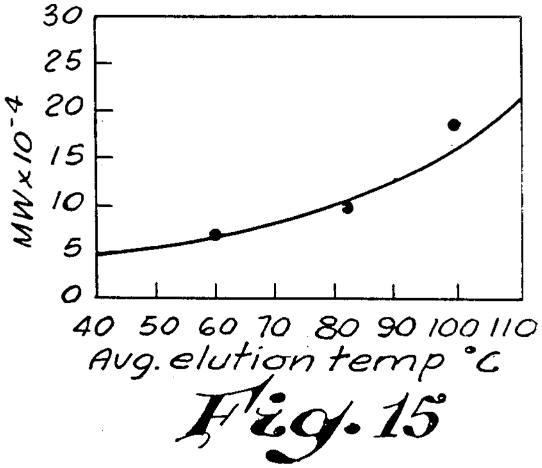
FIG. 15 is a plot of the data of Table III, plotting molecular weight$\times 10^{-4}$ (abscissa) against elution temperature (ordinate).

The ATREF crystallinity distribution data for ethylene/octene copolymer B, a different lot of the same type resin in Example 3, is presented in FIG. 13. The general features of the curve profile are very similar, though not identical, to those of FIG. 11. Table VII and FIGS. 14 and 15 show data on molecular weight of the ATREF fractions of this second resin. The segments marked off in FIG. 13 show the temperature range (ΔT approx. 5° C.) over which fractions were retained. GPC curve overlays of the whole polymer and ATREF fractions 9 and 18 (FIG. 14) indicate a trend toward higher average molecular weights as the fraction of crystallinity increases (i.e. as octene content decreases). FIG. 15 shows this same trend in terms of the molecular weight average (Mw) of the ATREF fractions.

It should be noted that while each ATREF fraction was relatively homogeneous in terms of octene content—that is, narrow in short chain branch distribution—it was broad in molecular weight distribution. Stated another way, each individual fraction contained polymer molecules having the same relative amount of octene incorporated, but those same molecules represented a broad range of polymer chain lengths (molecular weights.) This obervation points out as well the fractionation mechanism operating in ATREF is effecting a separation based primarily on crystallinity (which is, in turn, governed by the degree of short chain branching) and not molecular weight.

TABLE VII

| MW DATA ON ETHYLENE/OCTENE COPOLYMER ATREF FRACTIONS | | | | | |
|---|---|---|---|---|---|
| FRACTION (ATREF 13) | COLUMN ELUTION TEMPERATURE, °C. | $\overline{M}n \times 10^{-4}$ | $\overline{M} \times 10^4$ | MP $\times 10^{-4}$ | $\overline{M}w/\overline{M}n$ |
| 4 | 35–40 | 1.76 | 8.29 | 1.16 | 4.71 |
| 9 | 57–62 | 1.75 | 7.20 | 2.81 | 4.10 |
| 14 | 79–84 | 5.25 | 10.6 | 4.48 | 4.11 |
| 18 | 97–101 | 1.69 | 18.4 | 6.20 | 3.50 |
| WHOLE POLYMER | — | 1.69 | 10.2 | 2.77 | 6.02 |

EXAMPLE 5

Figure 16:
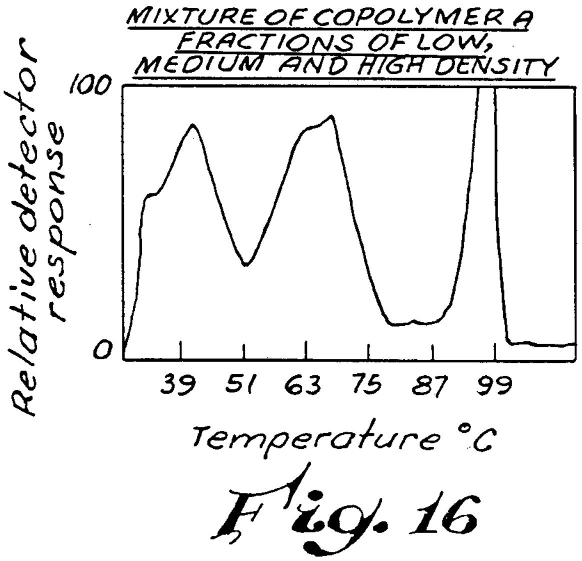
FIG. 16 is a graph of ATREF crystallinity distributions obtained from a mixture of three preparative TREF fractions (Example 5) of copolymer A. Relative concentration is plotted on the ordinate and elution temperature is plotted on the abscissa.

This is an example of ATREF of a mixture of preparative TREF fractions of copolymer A. The mixture consisted of equal weights of preparative fractions 2 ($18CH_3/1000$ C, 40° to 45° C. elution T), 7 ($13CH_3/1000$ C, 65° to 70° C. elution T), and 14 ($0.9CH_3/1000$ C, 100°–105° C. elution T). This mixture 0.5 g total polymer) was fractionated under the same conditions as Examples 1 to 4. The purpose of the trial was to gain information on how narrow a crystallinity distribution was being achieved by preparative TRET and whether the ATRET procedure could in fact show good separation of a mixture of three discrete crystallinity ranges. FIG. 16 shows the ATREF crystallinity distribution obtained from the mixture. The preparative method of fractionation resulted in a fairly broad range of crystallinities within fractions 2 (low crystallinity, high octene content) and 7 (intermediate crystallinity, average octene content). Fraction 14 (high crystallinity, low octene content) appeared to have the narrowest range of crystallinity of the three. It should be noted that the preparative TREF procedure is not expected to produce ideally narrow crystallinity distributions for any fraction since the fractions are routinely collected over 5° C. temperature intervals. The curve profile of FIG. 15 also indicates that the ATREF procedure is capable of resolving a mixture of different crystallinities.

Table VIII below lists certain characteristics of the polymer samples of Examples 1 to 4 above.

TABLE VIII

| ATREF SAMPLES | | | |
|---|---|---|---|
| Ex. | Resin | MI | Density, g/cc |
| 1 | HDPE | 10.0 | 0.962 |
| 2 | LDPE | 2.0 | 0.922 |
| 3 | Ethylene/Octene | Copolymer A | |
| 2.3 | 0.917 | | |
| 4 | Ethylene/Octene Copolymer B | 2.3 | 0.918 |

EXAMPLE 6

Figure 22:
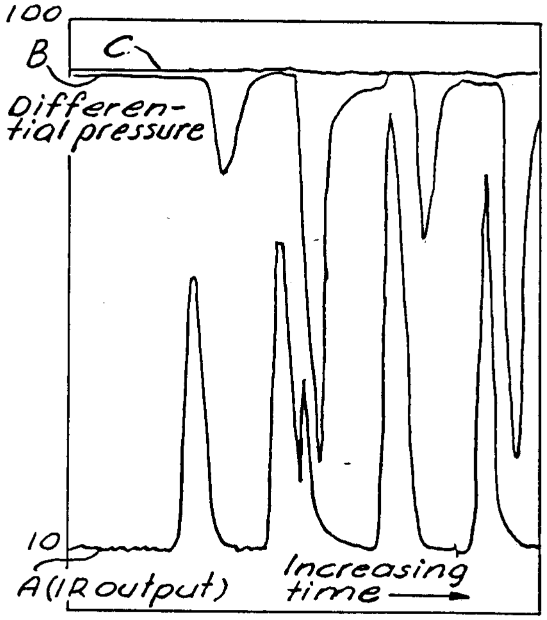
FIG. 22 is a plot for the concentration versus mass detector response for the Wilkes Infrared Detector.

To calibrate the infrared detector so that a concentration can be assigned to each response, three different concentrations of the same ethylene/octene resin described in Examples 3 and 5 were prepared. The entries of Table IX summarize the preparation of these solutions. Solution A was the starting solution, 0.620 weight percent polymer. It was kept in an oven at 150° C. and added to differing proportions of fresh 1,2,4-trichlorobenzene to obtain the diluted weight percent values in the third column. Sequential injections of these solutions are depicted in FIG. 22. The second injection was too concentrated and was reinjected in the fourth position (lower trace) of FIG. 22 with the sensitivity reduced by a factor of 2.5. Table X summarizes the actual readings measured by the computer at 75 second intervals as described in previous sections. The total area of each peak was estimated by using a trapezoid approximation. The area of each element divided by the total area (area percent) times g, the weight injected, divided by 1.25 cc=((1 cc/60 sec) 75 sec) is the average concentration of the element at room temperature. This concentration was corrected for the expansion of TCB to 135° C. Thus, the ratio of the densities at 135° C. and 25° C. was multiplied by each concentration. Finally, this concentration must be converted to g/dl. The result of all of these corrections is shown in the following equation:

average concentration = area of element/(total Area * sampling interval *flow rate *density correction *0.01 *dl/cc*) *weight injected $$\bar{c}_i = r_i \div \left( \sum_{J=1}^{11} \bar{r}_j \, 1.25 \cdot 1.0 \cdot (1.4527 \div 1.3186) \cdot 0.01 \right) \cdot g$$

The summation of $\bar{r}j$ is just the total area. The value of $\bar{r}_i$ is the average height of the curve from baseline (the area of a trapezoid) for element i, which is bounded by the ith and the i+1th measurement. The correlation of the calculated concentration for each interval versus the average height was very good, establishing that the inferred concentrations are reliable.

TABLE IX

Solution A = 0.62 wt. % ethylene/octene copolymer A
Solution B = pure 1,2,4-trichlorobenzene performed hot (>135° C.)

| Sample No. | A Grams | B Grams | Weight Fraction A/(A + B) | Weight of Polymer Injected (g) (TCB in sample loop = 4.632 g) |
|---|---|---|---|---|
| 1 | 1.026 | 21.24 | 0.000285 (× 4.632) | 0.00132 |
| 2 | 3.814 | 18.50 | 0.000106 (× 4.632) | 0.00492 |
| 3 | 1.664 | 19.94 | 0.00478 (× 4.632) | 0.00222 |

TABLE X $\bar{r}_i = \frac{1}{2}(r_i + r_{i+1})$

| Sample 1 | | | Sample 2 | | | Sample 3 | | |
|---|---|---|---|---|---|---|---|---|
| $r_{i+1}$ | $\bar{r}_i$(a/d) | $c_i$(g/dl)(×10²) | $r_{i+1}$ | $\bar{r}_i$(a/d) | $c_i$(g/dl)(×10²) | $r_{i+1}$ | $\bar{r}_i$(a/d) | $c_i$(g/dl)(×10²) |
| 2 | 1 | 0.019 | 13 | 6.5 | 0.114 | 64 | 32 | 0.517 |
| 77 | 36.5 | 0.683 | 141 | 77 | 1.36 | 232 | 232 | 2.39 |
| 163 | 117 | 2.19 | 249 | 195 | 3.45 | 295 | 263 | 4.25 |
| 177 | 170 | 3.18 | 229 | 239 | 4.23 | 222 | 258.2 | 4.17 |
| 119 | 148 | 2.77 | 124 | 176.5 | 3.12 | 109 | 165.5 | 2.67 |
| 53 | 86 | 1.61 | 48 | 86 | 1.52 | 43 | 76 | 1.23 |
| 20 | 36.5 | 0.683 | 19 | 33.5 | 0.529 | 17 | 30 | 0.484 |
| 8 | 14 | 0.262 | 10 | 14.5 | 0.256 | 9 | 13 | 0.210 |
| 3 | 5.5 | 0.103 | 5 | 7.5 | 0.133 | 4 | 6.5 | 0.105 |
| 1 | 2 | 0.037 | 2 | 3.5 | 0.062 | 3 | 3.5 | 0.057 |
| 0 | 0.5 | 0.009 | 0 | 1 | 0.018 | 0 | 1.5 | 0.24 |
| Total | 617 | | | 2016 | | 998 | | |

EXAMPLE 7

Figure 23:
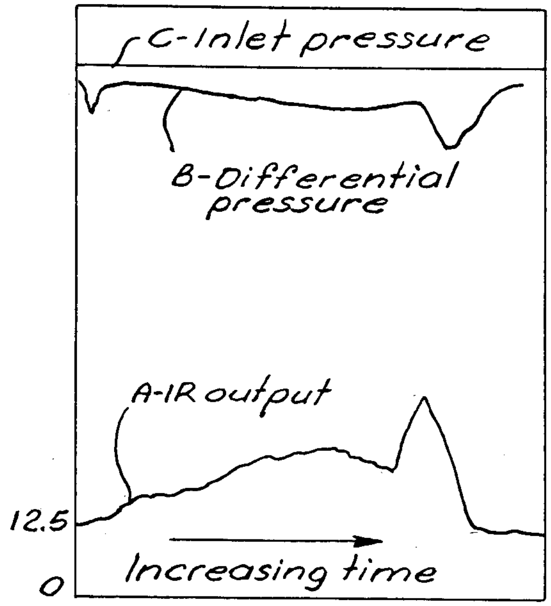
FIG. 23 is a plot of the raw data for a typical ATREF run using on-line high temperature continuous viscometry
Figure 24:
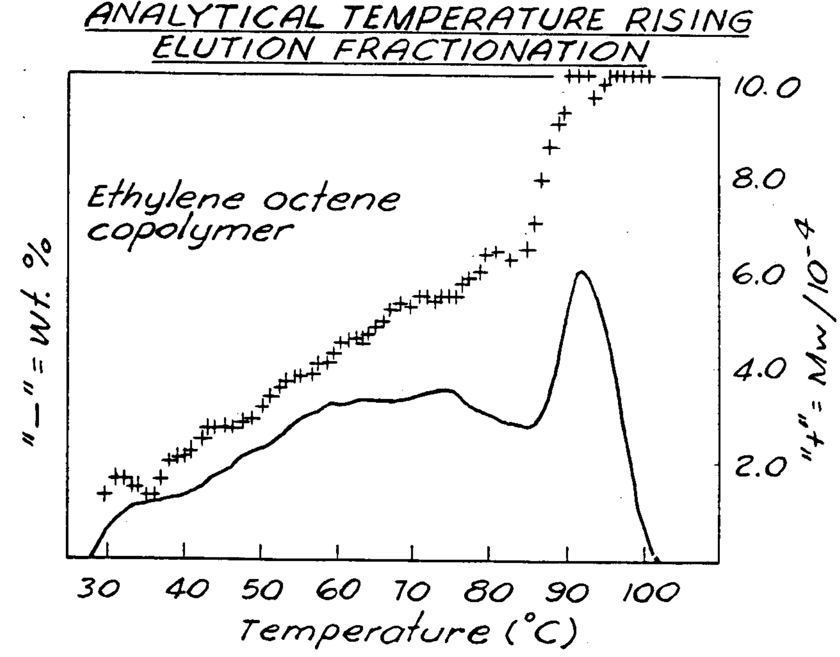
FIG. 24 is a plot of the computer output of normalized elution temperature data overlayed with instantaneous viscosity average molecular weights.

The starting solution, A, of the previous example was prepared for analysis in the usual manner (see previous examples). After the data acquisition was completed, the raw curve was examined. FIG. 23 is the raw data from the two detector system. The lower trace is the usual mass detector response, in this case from the Wilkes infrared single beam detector set to 3.46μ. The next race up is the differential pressure drop as measured by the Viskotek viscometer, which was downline by 108 sec. from the IR detector. The recorded output for the differential pressure trace was 200 mv full scale and the Viskotek attenuation was set to 5.0 pascals/mv. The A/D numbers were 10/mv (a count of 10 equals 1 mv signal). The nearly straight line at the top is the inlet pressure, which was constant at 19.9 Kpascals. The data reduction is summarized in FIG. 24 and Table IV. In FIG. 24, the normalized weight percent versus temperature plot is the solid line and the "pluses" are the calculated viscosity average molecular weight for each A/D measurement. The tabulated values shown in Table IV are given in the far right column. The trend in the data was in essential agreement with earlier examples.

The values were somewhat lower than the weight averages in FIG. 15, but this is expected since these are viscosity average molecular weights. The range in molecular weights suggest a fairly broad distribution, and this is again supported by the earlier SEC data. Most importantly though, the trend of low molecular weight to high molecular weight with elution temperature was dramatically demonstrated. Finally, the whole polymer intrinsic viscosity, as calculated from the weight average of the incremental intrinsic viscosity was in agreement with an independent measurement of 1.345. This last value was obtained by using the Viskotek in the conventional manner as described by Haney, M. A., "A New Differential Viscometer—Part one," *American Laboratory* 17(3), 1985.

The foregoing discussion supports the proposition that on-line high temperature continuous viscosity is a valuable aid in probing branching distribution as it relates to molecular weight.

Having now fully described the invention, it will be apparent to one of skill in the art that many obvious modifications and variations exist which do not affect or change the scope thereof.

What is claimed is:

1. A method for analyzing a solution of a crystalline or a semi-crystalline polymer sample comprising the steps of:

(a) precipitating the polymer sample solution over a cooling temperature gradient to produce a precipitated polymer sample, said precipitated polymer sample being precipitated as a function of its crystallinity or branching configuration or density;

(b) eluting said precipitated polymer sample over a heating temperature gradient to produce successive fractions of a fractionated polymer sample solution;

(c) successively measuring the instantaneous concentration of the successive fractions of said fractionated polymer sample solution, at a first temperature in excess of a precipitation temperature of said fractionated polymer sample solution, to produce instantaneous concentration c data;

(d) successively measuring the instantaneous specific viscosity of the successive fractions of said fractionated polymer sample solution, at a second temperature in excess of a precipitation temperature of said fractionated polymer sample solution, to produce instantaneous specific viscosity Spv data; and (e) determining the instantaneous intrinsic viscosity Intv of the successive fractions of said fractionated polymer sample solution in accordance with said instantaneous concentration c data from step (c) and said specific viscosity Spv data from step (d).

2. The method of claim 1, wherein step (a) comprises the steps of:

(1) adding the solution of polymer sample into a column; and (2) precipitating said solution of polymer sample in said column over said cooling temperature gradient to produce said precipitated polymer sample.

3. The method of claim 2, wherein step (2) comprises the step of cooling said column in an oil bath to produce said cooling temperature gradient.

4. The method of claim 2, wherein step (2) comprises the step of cooling said column in an oven to produce said cooling temperature gradient.

5. The method of claim 1, wherein step (b) comprises the steps of:

(1) raising the temperature of a column over said heating temperature gradient; and (2) eluting said precipitated polymer sample from said column to produce said fractionated polymer sample solution.

6. The method of claim 5, wherein step (2) comprises the step of producing a continuous stream of fractionated polymer sample solution from said precipitated polymer sample.

7. The method of claim 5, where step (1) comprises heating said column in an oil bath to produce said heating temperature gradient.

8. The method of claim 5, wherein step (1) comprises heating said column in an oven to produce said heating temperature gradient.

9. The method of claim 1, wherein said first temperature of step (c) is substantially equal to said second temperature of step (d).

10. The method of claim 1, wherein the instantaneous concentration of the successive fractions of said fractionated polymer sample solution of step (c) is measured optically.

11. The method of claim 10, wherein said optical measurement step is performed in the infrared range.

12. The method of claim 10, wherein said optical measurement step is performed using differential refractometry.

13. The method of claim 1, wherein the instantaneous specific viscosity of the successive fractions of said fractionated polymer sample solution of step (d) is measured by determining a pressure drop across a capillary tube.

14. The method of claim 1, further comprising the step (f) of determining the instantaneous viscosity average molecular weight $Mv_i$ of the various fractions in accordance with said instantaneous intrinsic viscosity Intv.

15. The method of claim 1, further comprising the step (f) of determining the instantaneous viscosity average molecular weight in accordance with the following equation:

$$Mv_i = \left(\frac{Intv}{K}\right)^{1/a}$$

Where:

$Mv_i$=instantaneous viscosity average molecular weight;

Intv=instantaneous intrinsic viscosity;

K=the intercept in the Mark-Houwink-Sakurada relationship; and a=the exponent in the Mark-Houwink-Sakurada relationship.

16. The method of claim 15, where step (f) comprises the step of assigning the following values:

$K=6.23\times10^{-4}$ a=0.695.

17. Apparatus for analyzing a solution of a crystalline or semi-crystalline polymer sample comprising:

(a) means for precipitating the polymer sample solution over a cooling temperature gradient to produce a precipitated polymer sample, said precipitated polymer sample being precipitated as a function of its crystallinity or branching configuration or density;

(b) means for eluting said precipitated polymer sample over a heating temperature gradient to produce successive fractions of a fractionated polymer sample solution;

(c) first means for successively measuring the instantaneous concentration of the successive fractions of said fractionated polymer sample solution, at a first temperature in excess of a precipitation temperature of said fractionated polymer sample solution, to produce instantaneous concentration c data;

(d) second means for successively measuring the instantaneous specific viscosity of the successive fractions of said fractionated polymer sample solution, at a temperature in excess of a precipitation temperature of said fractionated polymer sample solution, to produce instantaneous specific viscosity Spv data; and (e) third means for determining the instantaneous intrinsic viscosity Intv of the successive fractions of said fractionated polymer sample solution in accordance with said instantaneous concentration data c from said first means and said instantaneous specific viscosity data Intv from said second means.

18. The apparatus of claim 17, further comprising storage means, connected to said first means and said second means, for storing said instantaneous concentration c data and said instantaneous specific viscosity Spv data.

19. The apparatus of claim 18, further comprising retrieval means, connect to said storage means and said third means, for providing to said third means said instantaneous concentration c data and said instantaneous specific viscosity Spv data stored by said storage means.

20. The apparatus of claim 18, further comprising means for maintaining said first temperature of said first means and said second temperature of said second means at substantially the same value.

21. The apparatus of claim 18, wherein said second means comprises a capillary tube and means for determining pressure drop across said capillary tube.

22. The apparatus of claim 18, wherein said first means comprises optical means.

23. The apparatus of claim 22, wherein said optical means comprises infrared optical means.

24. The apparatus of claim 22, wherein said optical mean comprises differential refractometer means.

25. The apparatus of claim 18, wherein said means for eluting said precipitated polymer sample comprises a column.

26. The apparatus of claim 17, wherein said means for precipitating comprises oil bath means for producing said cooling temperature gradient.

27. The apparatus of claim 17, wherein said means for precipitating comprises oven means for producing said cooling temperature gradient.

28. The apparatus of claim 17, wherein said means for eluting comprises oil bath means for producing said heating temperature gradient.

29. The apparatus of claim 17, wherein said means for eluting comprises oven means for producing said heating temperature gradient.

30. The apparatus of claim 17, wherein said third means comprises means for determining said instantaneous intrinsic viscosity Intv in accordance with the equation Intv=Spv/c.

31. The apparatus of claim 17, further comprising fourth means, connected to said third means, for determining the instantaneous viscosity average molecular weight in accordance with said instantaneous intrinsic viscosity Intv.

32. The apparatus of claim 17, further comprising fourth means, connected to said third means, for determining the instantaneous viscosity average molecular weight in accordance with the equation $$Mv_i = \left(\frac{Intv}{K}\right)^{1/a},$$

where $Mv_i$ is equal to the instantaneous viscosity average molecular weight, K is the intercept of the Mark-Houwink-Sakurada equation, and a is the exponent of the Mark-Houwink-Sakurada equation.

* * * * *

UNITED STATES PATENT AND TRADEMARK OFFICE
CERTIFICATE OF CORRECTION

PATENT NO. : 4,798,081

DATED : Jan. 17, 1989

INVENTOR(S) : Lonnie G. Hazlitt, Daniel G. Moldovan

It is certified that error appears in the above-identified patent and that said Letters Patent is hereby corrected as shown below:

Col. 1, line 53, delete "o" and insert --of--.

Figure 12:
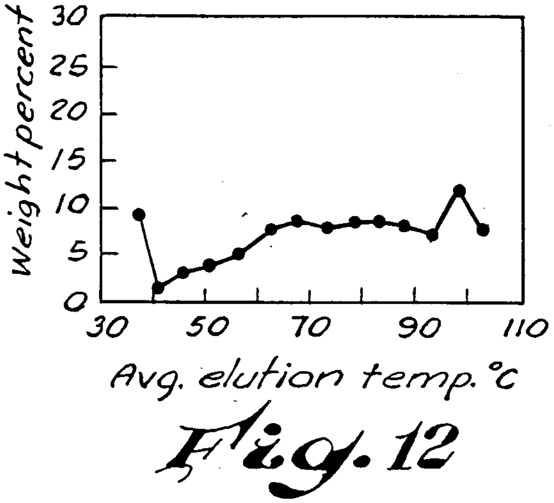
FIG. 12 is a graph of preparative TREF crystallinity distribution for copolymer A. Relative concentration is plotted on the ordinate: elution temperature is plotted on the abscissa.

Col. 2, line 5, after "increased" insert --.--.
Col. 2, line 57, delete "a" and insert --an--.
Col. 6, line 51, delete "numberal" and insert --numeral--.
Col. 7, line 34, delete ";" and insert --:--.
Col. 7, line 36, after "sure" insert --.--.
Col. 11, line 51, delete "21" and insert --218--.
Col. 16, line 41, delete "$r_i$" and insert --$\bar{r}_i$--, and also in Col. 16, line 50.
Col. 17, line 63, (Fig. 12a), after [η] insert -- = --. (equal symbol)
Col. 19, line 54, delete "Clocking", both instances, and insert --Clockerq--, both instances.
Col. 20, line 60, after "Clocks", insert --.--.
Col. 21, line 34, delete "2550" and insert --2150--.
Col. 28, line 25, delete "substracted" and insert --subtracted--.
Col. 30, line 32, after "decreases", insert --.--.
Col. 32, line 32, delete "obervation" and insert --observation--.
Col. 38, line 6, Claim 24, delete "mean" and insert --means--.

Signed and Sealed this

Seventeenth Day of October, 1989

Attest:

DONALD J. QUIGG

Attesting Officer

Commissioner of Patents and Trademarks